(12) United States Patent
Igarashi

(10) Patent No.: US 11,813,387 B2
(45) Date of Patent: Nov. 14, 2023

(54) BLOOD COMPONENT COLLECTION BAG SET WITH INTERNAL PRESSURE DETECTION AND METHOD

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 672 days.

(21) Appl. No.: 16/620,960

(22) PCT Filed: Jun. 12, 2018

(86) PCT No.: PCT/JP2018/022348
§ 371 (c)(1),
(2) Date: Dec. 10, 2019

(87) PCT Pub. No.: WO2018/230545
PCT Pub. Date: Dec. 20, 2018

(65) Prior Publication Data
US 2020/0197583 A1  Jun. 25, 2020

(30) Foreign Application Priority Data
Jun. 16, 2017  (JP) .................................. 2017-118851

(51) Int. Cl.
*A61M 1/02* (2006.01)
*A61M 1/34* (2006.01)

(52) U.S. Cl.
CPC ......... *A61M 1/0218* (2014.02); *A61M 1/3496* (2013.01); *A61M 2202/0415* (2013.01);
(Continued)

(58) Field of Classification Search
CPC .... A61M 1/0218; A61M 1/30; A61M 1/3496; A61M 1/38; A61M 2202/0415;
(Continued)

(56) References Cited

U.S. PATENT DOCUMENTS

| | | | |
|---|---|---|---|
| 6,200,287 B1* | 3/2001 | Keller | A61M 1/3693 604/4.01 |
| 6,280,406 B1 | 8/2001 | Dolecek et al. | |
| 2013/0150225 A1 | 6/2013 | Katz et al. | |

FOREIGN PATENT DOCUMENTS

| | | |
|---|---|---|
| JP | S58-005443 | 1/1983 |
| JP | 2001-504748 | 4/2001 |

(Continued)

OTHER PUBLICATIONS

International Searching Authority; International Search Report and Written Opinion, PCT/JP2018/022348, dated Sep. 3, 2018, 10 pages.
(Continued)

*Primary Examiner* — Dirk R Bass
(74) *Attorney, Agent, or Firm* — Sheridan Ross P.C.

(57) ABSTRACT

A flow path is formed in a cassette body of a blood component collection cassette. The cassette body includes a bulging structure in which at least a portion of the flow path is formed. A first gripped member, which is configured to be gripped by a first gripping member provided on a centrifugal separation device, is disposed on one surface of the bulging structure in a thickness direction thereof. A second gripped member, which is configured to be gripped by a second gripping member to which a load detection unit that is provided on the centrifugal separation device is fixed, is disposed on another surface of the bulging structure in the thickness direction thereof.

20 Claims, 16 Drawing Sheets

(52) U.S. Cl.
CPC .............. *A61M 2205/125* (2013.01); *A61M 2205/3327* (2013.01); *A61M 2205/3331* (2013.01); *A61M 2205/7545* (2013.01); *A61M 2207/00* (2013.01)

(58) Field of Classification Search
CPC ........ A61M 2205/12; A61M 2205/125; A61M 2205/3327; A61M 2205/3331; A61M 2205/7545; A61M 2207/00
See application file for complete search history.

(56) References Cited

FOREIGN PATENT DOCUMENTS

| | | |
|---|---|---|
| JP | 2010-158369 | 7/2010 |
| WO | 9900305 A1 | 5/2007 |

OTHER PUBLICATIONS

Official Action (with English translation) for Japan Patent Application No. 2019-565962, dated Mar. 1, 2022, 10 pages.

\* cited by examiner

BLOOD COMPONENT COLLECTION BAG SET WITH INTERNAL PRESSURE DETECTION AND METHOD

TECHNICAL FIELD

The present invention relates to a blood component collection cassette, a blood component collection kit, a blood component collection system, and a flow path internal pressure detection method.

BACKGROUND ART

In blood donation in recent years, in addition to whole blood collection in which whole blood is collected from blood donors, component blood sampling (apheresis) has been performed in which the burden on the blood donor's body is made lighter. Component blood sampling is a blood collection method in which a blood component collection system (apheresis system) is used, whereby only specific blood components are collected from whole blood, and the remaining components are returned again into the donor's body.

Japanese Laid-Open Patent Publication No. 2013-514863 (PCT) discloses a blood component collection system in which blood platelets are collected by centrifugally separating whole blood that is extracted from a blood donor. Such a blood component collection system includes a blood collection circuit set, which forms a circuit through which blood or blood components to be treated flow, and a centrifugal separation device (blood component separating device) on which the blood collection circuit set is mounted.

The blood collection circuit set is equipped with a blood collection line having a blood collecting needle, a band-shaped channel (separator) into which whole blood is introduced, a plurality of bags for accommodating blood components, etc., and a cassette connected through a plurality of tubes to the bags. A plurality of flow paths, including a line for introducing blood from a blood donor, a line for transferring the blood components into a bag, a blood returning line for returning uncollected blood components to the donor, etc., are formed in the cassette. When used, the cassette is mounted in a mounting unit disposed in the blood component separating device.

SUMMARY OF INVENTION

In such a blood component collection system, in order to ascertain whether or not the blood component separating device is operating properly, it is necessary to measure and monitor the pressure (circuit internal pressure) inside the blood collection circuit. In regards to the circuit internal pressure, it is desirable to be capable of measuring both a negative pressure and a positive pressure, and that the circuit internal pressure can be measured accurately even in a low pressure region.

The present invention has been devised taking into consideration the aforementioned problem, and has the object of providing a blood component collection cassette, a blood component collection kit, a blood component collection system, and a flow path internal pressure detection method, by which it is possible to accurately measure a circuit internal pressure in both negative pressure and positive pressure regions.

In order to realize the aforementioned object, according to one aspect of the present invention, there is provided a blood component collection cassette including a cassette body with a flow path formed therein, and which is configured to be installed in a blood component separating device having a load detection unit, wherein the cassette body includes a bulging structure having a bulging portion for pressure measurement, the bulging portion for pressure measurement bulging in a cassette thickness direction on at least one surface of the cassette body in the cassette thickness direction, the bulging structure is formed of a soft material, the bulging structure contains in the interior thereof at least a portion of the flow path, on one surface of the bulging structure in a thickness direction thereof, there is provided a first gripped member which is configured to be gripped by a first gripping member provided on the blood component separating device, and on another surface of the bulging structure in the thickness direction thereof, there is provided a second gripped member which is configured to be gripped by a second gripping member to which the load detection unit is fixed.

According to the aspect of the present invention, by using the blood component collection cassette, the load detection unit, which is provided on the blood component separating device, can accurately measure the circuit internal pressure (negative pressure and positive pressure), without applying an initial reaction force for pressure measurement to the cassette body. More specifically, the first gripped member provided on the bulging portion for pressure measurement is gripped by the first gripping member that is provided on the blood component separating device, and the second gripped member provided on the bulging portion for pressure measurement is gripped by a second gripping member that is provided on the blood component separating device. Therefore, both in the case of a positive pressure as well as in the case of a negative pressure, the circuit internal pressure acts on the load detection unit that is fixed to the second gripping member. Accordingly, the circuit internal pressure can be measured on the basis of the load detected by the load detection unit.

The cassette body preferably includes a first sheet and a second sheet which are formed of a soft material, the first sheet and the second sheet preferably are stacked in the thickness direction and are bonded to each other, and the flow path preferably is formed between the first sheet and the second sheet.

Since the blood component collection cassette can be manufactured by joining the first sheet and the second sheet that are made of a soft material, the cassette can be manufactured at a lower cost, as compared with a conventional cassette made of a hard resin and which is manufactured by injection molding.

The first gripped member preferably is fixed to the one surface of the bulging structure, and is a first engagement member having an engagement protrusion or an engagement groove which is configured to engage with the first gripping member, and the second gripped member preferably is fixed to the other surface of the bulging structure, and is a second engagement member having an engagement protrusion or an engagement groove which is configured to engage with the second gripping member.

In accordance with this configuration, it is possible for the first gripped member and the second gripped member to be gripped with a sufficient gripping force respectively by the first gripping member and the second gripping member, thus making it possible to stably measure the circuit internal pressure.

The cassette body is preferably formed therein with another portion of the flow path other than the portion of the flow path contained within the bulging structure, and includes a flow path forming convex wall portion that protrudes in the cassette thickness direction. In addition, a protruding height of the bulging structure from a plate-shaped base portion of the cassette body preferably is greater than a protruding height of the flow path forming convex wall portion from the plate-shaped base portion, and a width of the bulging structure preferably is greater than a width of the flow path forming convex wall portion.

By this configuration, since the bulging structure is easily deformed in accordance with the circuit internal pressure, the measurement accuracy of the circuit internal pressure can be improved.

The bulging portion for pressure measurement preferably bulges in a dome shape from the plate-shaped base portion.

In accordance with this configuration, the manner in which deformation of the bulging structure follows with respect to the circuit internal pressure is improved, and thus the measurement accuracy of the circuit internal pressure can be further improved.

The bulging portion for pressure measurement preferably is formed in a circular shape as viewed in the cassette thickness direction.

In accordance with this configuration, it is possible to further improve the manner in which deformation of the bulging structure follows with respect to the circuit internal pressure.

The first gripped member and the second gripped member preferably are disposed on a central part of the bulging portion for pressure measurement.

In accordance with this configuration, it is possible to further improve the measurement accuracy of the circuit internal pressure.

The flow path preferably includes a first line in which a filter member configured to trap an agglutinated substance made up of blood components is arranged, and a second line in which the filter member is not arranged. In addition, the filter member preferably is arranged inside the bulging structure.

In accordance with this configuration, since the bulging structure also serves to provide a filter function, the filter member can be arranged in the cassette without adding complexity to the flow path structure.

The cassette body may include a flow path forming member configured to form the flow path and including the bulging structure therein, and a cassette base part made of a hard material and configured to support the flow path forming member.

Further, according to another aspect of the present invention, there is provided a blood component collection system including a blood component separating device including a first gripping member, a second gripping member, and a load detection unit fixed to the second gripping member, and a blood component collection cassette configured to be installed in the blood component separating device, wherein the blood component collection cassette includes a cassette body with a flow path formed therein, the cassette body includes a bulging structure having a bulging portion for pressure measurement, the bulging portion for pressure measurement bulging in a cassette thickness direction on at least one surface of the cassette body, the bulging structure is formed of a soft material, the bulging structure contains in the interior thereof at least a portion of the flow path, on one surface of the bulging structure in a thickness direction thereof, there is provided a first gripped member which is configured to be gripped by the first gripping member, on another surface of the bulging structure in the thickness direction thereof, there is provided a second gripped member which is configured to be gripped by the second gripping member, and the blood component separating device acquires a pressure in the interior of the flow path on the basis of a load detected by the load detection unit.

In the above-described blood component collection system, the cassette body preferably includes a first sheet and a second sheet which are formed of a soft material, the first sheet and the second sheet preferably are stacked in a thickness direction and are bonded to each other, and the flow path preferably is formed between the first sheet and the second sheet.

In the above-described blood component collection system, the first gripping member preferably has an engagement groove or an engagement protrusion which is configured to engage with the first gripped member, and the second gripping member preferably has an engagement groove or an engagement protrusion which is configured to engage with the second gripped member.

In accordance with this configuration, it is possible for the first gripped member and the second gripped member to be gripped respectively with a sufficient gripping force by the first gripping member and the second gripping member, thus making it possible to stably measure the circuit internal pressure.

In the above-described blood component collection system, the blood component separating device preferably includes a cassette holder which is configured to hold the blood component collection cassette, and the cassette holder preferably includes an attachment base provided with a cassette mounting groove having a shape that corresponds to an outer peripheral shape of the cassette body, and a lid which is configured to be opened and closed with respect to the attachment base.

In accordance with this configuration, it is possible to easily attach the blood component collection cassette to a predetermined position of the blood component separating device, thereby improving workability when attaching the blood component collection cassette.

In the above described blood component collection system, preferably, the first gripping member is disposed at a position fixed with respect to the attachment base, and the second gripping member is arranged face-to-face with the first gripping member.

In accordance with this configuration, accompanying attachment of the blood component collection cassette to the cassette mounting groove, the first gripped member is gripped by the first gripping member, together with the second gripped member being gripped by the second gripping member, and therefore, workability when attaching the blood component collection cassette can be further improved.

In the above-described blood component collection system, the attachment base preferably includes an opening configured to receive at least a part of the bulging portion for pressure measurement, and a slit configured to communicate with the opening and allow passage of the second gripped member therethrough.

In accordance with this configuration, it is possible to further simplify the attachment of the blood component collection cassette to the cassette mounting groove.

Further, according to still another aspect of the present invention, there is provided a blood component collection kit which is configured to be installed in a blood component separating device having a load detection unit, and is equipped with a flow path in which blood is delivered by operation of the blood component separating device, wherein the blood component collection kit includes a bulging structure having a bulging portion for pressure measurement, the bulging portion for pressure measurement bulging in at least one direction of an axis perpendicular to a delivery direction of the flow path, the bulging structure is formed of a soft material, the bulging structure contains in the interior thereof at least a portion of the flow path, on one surface of the bulging structure in a thickness direction thereof, there is provided a first gripped member which is configured to be gripped by a first gripping member provided on the blood component separating device, and on another surface of the bulging structure in the thickness direction thereof, there is provided a second gripped member which is configured to be gripped by a second gripping member to which the load detection unit is fixed.

Further, according to yet another aspect of the present invention, there is provided a flow path internal pressure detection method of detecting an internal pressure of a flow path of a blood component collection cassette installed in a blood component separating device for collecting blood components, wherein the blood component collection cassette includes a cassette body with the flow path formed therein, the cassette body includes a bulging structure having a bulging portion for pressure measurement, the bulging portion for pressure measurement bulging in a cassette thickness direction on at least one surface of the cassette body, the bulging structure is formed of a soft material, and the bulging structure contains therein at least part of the flow path. In this case, the flow path internal pressure detection method includes a gripping step of gripping a first gripped member provided on one surface of the bulging structure in a thickness direction thereof, by a first gripping member that is provided on the blood component separating device, and gripping a second gripped member provided on another surface of the bulging structure in the thickness direction, by a second gripping member that is provided on the blood component separating device, a measurement step of measuring a load applied to a load detection unit fixed to the second gripping member, in a state in which the first gripped member is gripped by the first gripping member, the second gripped member is gripped by the second gripping member, and blood is being delivered to the bulging structure, and an internal pressure calculating step of calculating the internal pressure of the flow path on the basis of the measured load.

In accordance with the blood component collection cassette, the blood component collection kit, the blood component collection system, and the flow path internal pressure detection method of the present invention, with a simple and economical configuration, it is possible for the circuit internal pressure to be measured highly accurately in both negative pressure and positive pressure regions.

DESCRIPTION OF EMBODIMENTS

Preferred embodiments of a blood component collection cassette, a blood component collection kit, a blood component collection system, and a flow path internal pressure detection method according to the present invention will be presented and described in detail below with reference to the accompanying drawings.

Figure 1:
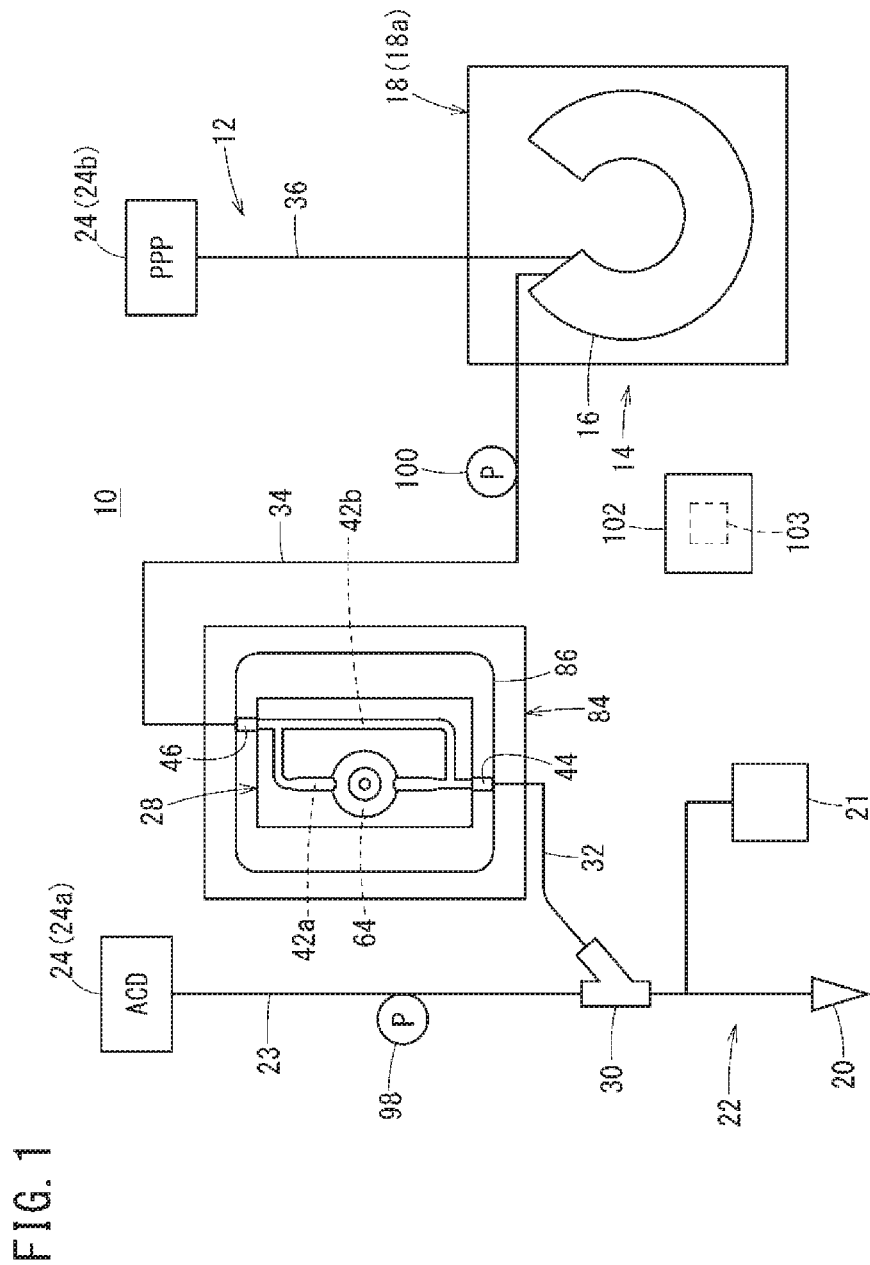
FIG. 1 is a schematic diagram of a blood component collection system according to an embodiment of the present invention.

As shown in FIG. 1, a blood component collection system 10 is constituted as a blood apheresis system, in which blood (whole blood) is continuously extracted from a blood donor and the blood is centrifuged outside the body, whereby a specific blood component (in the present embodiment, plasma (platelet-poor plasma: PPP)) is collected and the remaining blood components are returned to the blood donor.

First, an outline description will be given of the blood component collection system 10 shown in FIG. 1. The blood component collection system 10 comprises a blood collection circuit set 12 for enabling storage and flow of the blood components therein, and a centrifugal separation device 14 (blood component separating device) that applies a centrifugal force to the blood collection circuit set 12. The blood collection circuit set 12 includes a blood treatment unit 16 to which there is introduced whole blood that is removed from the blood donor, and the whole blood is centrifugally separated into a plurality of blood components. The centrifugal separation device 14 is equipped with a centrifuge unit 18 having a rotor 18a for applying a centrifugal force to the blood treatment unit 16. The blood treatment unit 16 is configured to be mounted in the centrifuge unit 18.

The blood collection circuit set 12 is discarded every time that it is used, in order to prevent contamination and ensure sanitation or good hygiene. The blood collection circuit set 12 comprises a blood collecting and blood returning unit 22 having a blood collecting needle 20 and an initial flow blood collecting bag 21, the blood treatment unit 16, a plurality of bags 24, and a blood component collection cassette 28 (hereinafter referred to as a "cassette 28") connected to these elements via tubes. The plurality of bags 24 include an ACD solution bag 24a containing an ACD solution which is an anticoagulant, and a PPP bag 24b for storing the plasma (platelet-poor plasma).

The blood collecting and blood returning unit 22 is connected to the ACD solution bag 24a and the cassette 28 via the tube connector 30. The ACD solution bag 24a is connected to the tube connector 30 via an ACD solution transfer tube 23.

The cassette 28 is connected to the blood collecting and blood returning unit 22 via a donor side tube 32, and is also connected to the blood treatment unit 16 via a treatment unit side tube 34. The blood treatment unit 16 is attached to the centrifuge unit 18 (rotor 18a) of the centrifugal separation device 14, and is configured in the form of a container in which blood can be introduced therein, flow therethrough, and flow out therefrom. The PPP bag 24b is connected to the blood treatment unit 16 via a PPP transfer tube 36.

Figure 2:
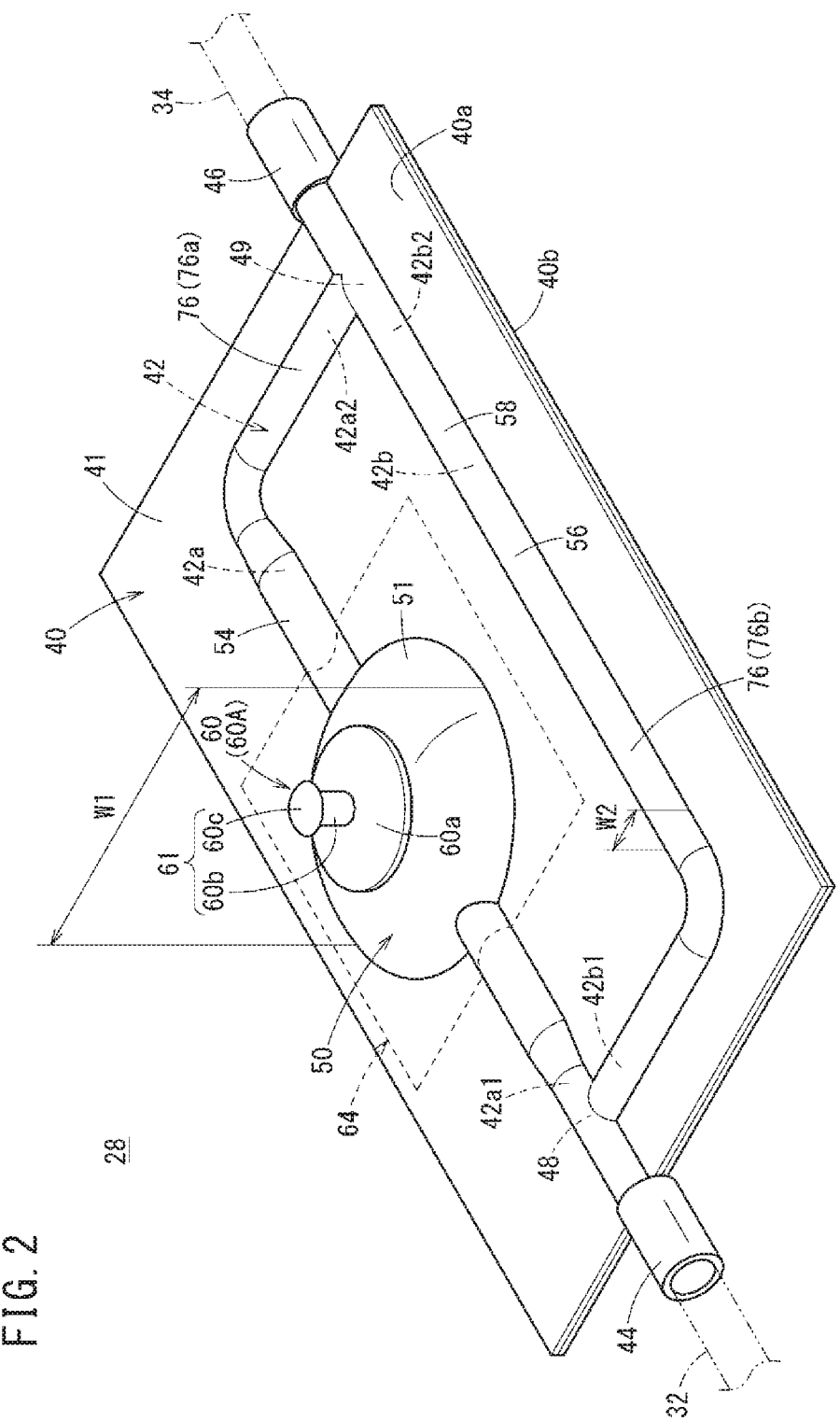
FIG. 2 is a perspective view of a blood component collection cassette.

As shown in FIG. 2, the cassette 28 is provided with a cassette body 40 in which a flow path 42 is formed. The cassette body 40 is formed in a rectangular shape as viewed in plan. The cassette body 40 includes a first sheet 40a and a second sheet 40b formed of a soft material. The first sheet 40a and the second sheet 40b are stacked in a thickness direction and are joined to each other.

As examples of the soft material that constitutes the first sheet 40a and the second sheet 40b, there may be cited vinyl chloride, polyolefin, polyurethane, and the like.

A flow path 42 is formed between the first sheet 40a and the second sheet 40b. As the means for joining the first sheet 40a and the second sheet 40b, there may be cited, for example, fusion bonding (high frequency fusion bonding, thermal fusion bonding, etc.), adhesion, and the like. Further, a first port member 44 and a second port member 46 are disposed on a peripheral edge portion of the cassette body 40. The first port member 44 is connected to one end side of the flow path 42. The second port member 46 is connected to another end side of the flow path 42. The donor side tube 32 and the treatment unit side tube 34 are connected respectively to the port members 44, 46.

The flow path 42 formed in the cassette body 40 includes a first line 42a in which a filter member 64 is arranged for removing an agglutinated substance made up of blood components (hereinafter referred to as "clotted blood"), and a second line 42b in which the filter member 64 is not disposed. One end side 42a1 of the first line 42a and one end side 42b1 of the second line 42b are connected via a first branching member 48. Another end side 42a2 of the first line 42a and another end side 42b2 of the second line 42b are connected via a second branching member 49. The first line 42a and the second line 42b extend at least partially in parallel with each other. The first branching member 48 and the second branching member 49 make up part of the flow path 42.

In the cassette body 40, even if there is no positive pressure acting within the flow path 42, the wall portions that form the flow path 42 bulge in convex shapes in a thickness direction (hereinafter referred to as a "cassette thickness direction") of the cassette 28 on both surfaces of the cassette body 40. Accordingly, the flow path 42 is a flow path which is opened in its natural state. When pressed by an external force, the wall portions can be elastically deformed in directions to close the flow path 42 at the pressed location thereof. The cassette body 40 includes a first line forming member 54 that forms the first line 42a, and a second line forming member 56 that forms the second line 42b.

Figure 3:
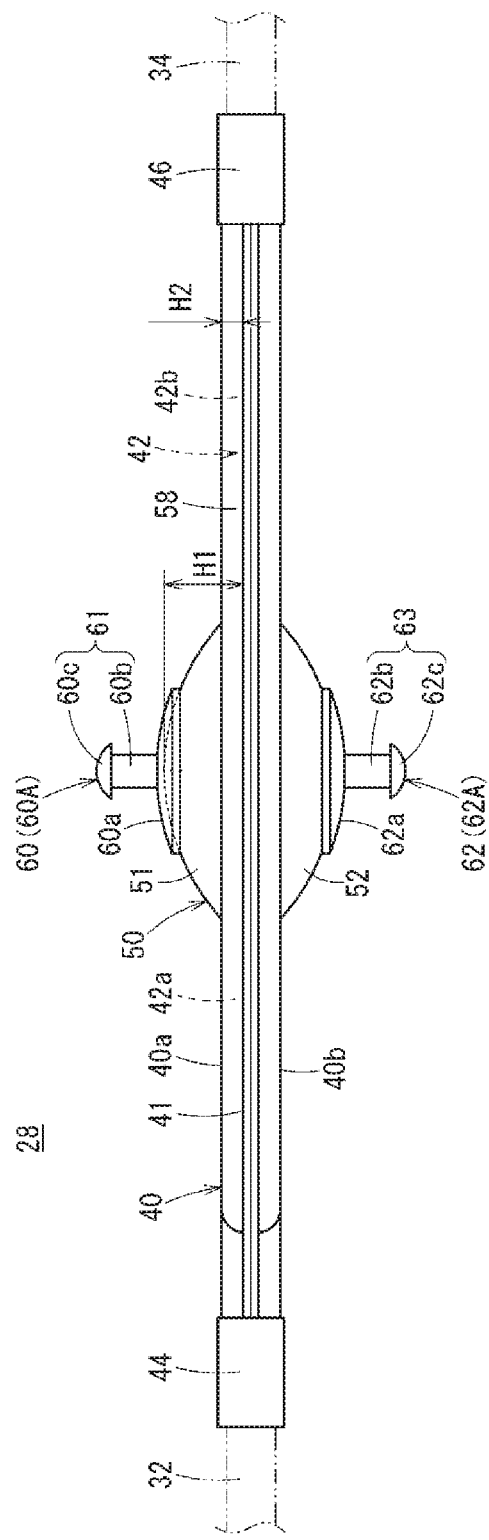
FIG. 3 is a side view of the blood component collection cassette.

As shown in FIG. 3, the cassette body 40 comprises a bulging structure 50 including a bulging portion for pressure measurement, which bulges outwardly in the cassette thickness direction from a plate-shaped base portion 41 (a portion within the cassette body 40 that does not bulge outwardly in a convex shape) on at least one side in the cassette thickness direction. At least a portion of the flow path 42 is formed inside the bulging structure 50. The bulging structure 50 makes up part of the first line forming member 54. According to the present embodiment, the bulging structure 50 includes a first bulging portion for pressure measurement 51 and a second bulging portion for pressure measurement 52, which bulge outwardly in the cassette thickness direction, respectively, on one side and another side of the cassette body 40. At least a portion of the flow path 42 is formed between the first bulging portion for pressure measurement 51 and the second bulging portion for pressure measurement 52.

As shown in FIG. 2, the cassette body 40 includes a flow path forming convex wall portion 58, which protrudes in the cassette thickness direction, together with forming in the interior thereof, from among the flow path 42, a flow path other than the flow path inside the bulging structure 50. The width W1 of the bulging structure 50 is greater than the width W2 of the flow path forming convex wall portion 58.

According to the present embodiment, the first bulging portion for pressure measurement 51 and the second bulging portion for pressure measurement 52 are formed in a circular shape when viewed from the cassette thickness direction. Alternatively, the first bulging portion for pressure measurement 51 and the second bulging portion for pressure measurement 52 may be formed in a non-circular shape (an elliptical shape, a polygonal shape, or the like) when viewed from the cassette thickness direction.

As shown in FIG. 3, the first bulging portion for pressure measurement 51 and the second bulging portion for pressure measurement 52 bulge in dome shapes in opposite directions from the plate-shaped base portion 41. The shapes and sizes of the first bulging portion for pressure measurement 51 and the second bulging portion for pressure measurement 52 may be the same or different from each other. The protruding height H1 of the bulging structure 50 from the plate-shaped base portion 41 is greater than the protruding height H2 of the flow path forming convex wall portion 58 from the plate-shaped base portion 41. Alternatively, the height H1 and the height H2 may be mutually of the same height. The height H1 also may be less than the height H2.

On the first bulging portion for pressure measurement 51, there is provided a first gripped member 60 which can be gripped by a later-described first gripping member 78 (see FIG. 6) disposed on the centrifugal separation device 14. On the second bulging portion for pressure measurement 52, there is provided a second gripped member 62 which can be gripped by a later-described second gripping member 80 (see FIG. 6) disposed on the centrifugal separation device 14. The first gripped member 60 is disposed in a central portion of the first bulging portion for pressure measurement 51. The second gripped member 62 is disposed in a central portion of the second bulging portion for pressure measurement 52.

Figure 4:
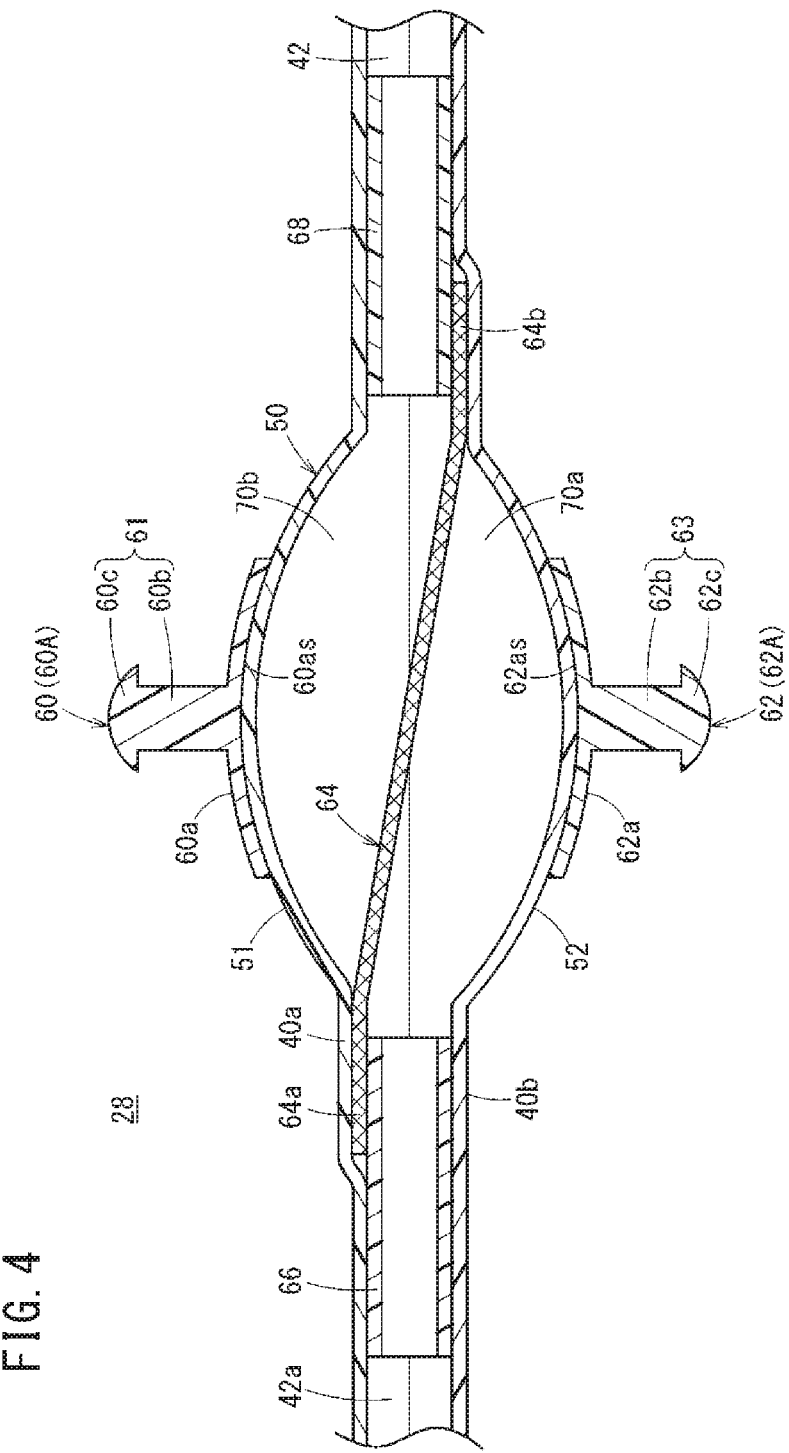
FIG. 4 is a cross-sectional view of the blood component collection cassette.

As shown in FIG. 4, according to the present embodiment, the first gripped member 60 is a first engagement member 60A which is fixed to the first bulging portion for pressure measurement 51 and which includes an engagement protrusion 61 capable of engaging with the first gripping member 78. The first engagement member 60A includes a fixed base 60a which is fixed to a top part of the first bulging portion for pressure measurement 51, a shaft portion 60b that protrudes from the fixed base 60a in the cassette thickness direction, and a flange-shaped engagement claw 60c provided on a projecting end of the shaft portion 60b. The shaft portion 60b and the engagement claw 60c constitute the engagement protrusion 61. The surface 60as of the fixed base 60a, which is fixed to the first bulging portion for pressure measurement 51, is in the form of a curved surface that is recessed in a spherical shape. The engagement claw 60c is formed with a larger diameter than that of the shaft portion 60b. Instead of the engagement protrusion 61, the first engagement member 60A may include an engagement groove that is capable of engaging with the first gripping member 78.

According to the present embodiment, the second gripped member 62 is a second engagement member 62A which is fixed to the second bulging portion for pressure measurement 52 and which includes an engagement protrusion capable of engaging with the second gripping member 80. The second engagement member 62A includes a fixed base 62a which is fixed to a top part of the second bulging portion for pressure measurement 52, a shaft portion 62b that protrudes from the fixed base 62a in the cassette thickness direction, and a flange-shaped engagement claw 62c provided on a projecting end of the shaft portion 62b. The shaft portion 62b and the engagement claw 62c constitute the engagement protrusion 63. The surface 62as of the fixed base 62a, which is fixed to the second bulging portion for pressure measurement 52, is in the form of a curved surface that is recessed in a spherical shape. The engagement claw 62c is formed with a larger diameter than that of the shaft portion 62b. The shaft portion 60b of the first engagement member 60A and the shaft portion 62b of the second engagement member 62A are arranged on the same axis. Instead of the engagement protrusion 63, the second engagement member 62A may include an engagement groove that is capable of engaging with the second gripping member 80.

As the constituent material of the first engagement member 60A and the second engagement member 62A, there may be cited, for example, vinyl chloride, cyclic polyolefin, polypropylene, polycarbonate, and the like. The first engagement member 60A and the second engagement member 62A may also be made from a metal material.

As shown in FIG. 4, a sheet mesh-shaped filter member 64 is disposed inside the bulging structure 50. A first tube member 66 and a second tube member 68 are disposed in the first line 42a at positions on both sides of the bulging structure 50. By the filter member 64, the internal space of the bulging structure 50 is partitioned into a first spatial region 70a that communicates with the first tube member 66, and a second spatial region 70b that communicates with the second tube member 68.

More specifically, the first tube member 66 is joined by fusion bonding or the like to the first sheet 40a and the second sheet 40b. One end side 64a of the filter member 64 is disposed between the first tube member 66 and the first sheet 40a. The first sheet 40a, the one end side 64a of the filter member 64, and the first tube member 66 are joined to each other mutually by fusion bonding or the like. The second tube member 68 is joined by fusion bonding or the like to the first sheet 40a and the second sheet 40b. Another end side 64b of the filter member 64 is disposed between the second tube member 68 and the second sheet 40b. The second sheet 40b, the other end side 64b of the filter member 64, and the second tube member 68 are joined to each other mutually by fusion bonding or the like.

As shown in FIG. 2, on the cassette 28, there are provided a plurality of clamp action members 76 (76a, 76b) on which a plurality of clamps 72 (72a, 72b) (see FIG. 5), which are provided in the centrifugal separation device 14, act. When the cassette 28 is installed in the centrifugal separation device 14, the clamp action members 76 abut against or are placed face-to-face with their corresponding clamps 72. More specifically, the clamp action member 76a is disposed more closely to the side of the second port member 46 than the bulging structure 50 within the first line forming member 54. The clamp action member 76a may also be disposed more closely to the side of the first port member 44 than the bulging structure 50 within the first line forming member 54. The clamp action member 76b is provided in the second line forming member 56.

Moreover, the flow path structure formed in the cassette 28, and the number and arrangement of the bags that are provided are not limited to the configurations shown and described above, but may be modified in accordance with the type of blood components to be collected, the method of use, and the like.

In a method for manufacturing the cassette 28 having the above-described configuration, there are included a molding step in which the first sheet 40a and the second sheet 40b are superimposed on each other, and the first sheet 40a and the second sheet 40b are fusion bonded together so as to form the flow path 42 between the first sheet 40a and the second sheet 40b, to thereby mold the cassette 28 equipped with the cassette body 40, and a sterilization step of sterilizing the cassette 28 obtained by the aforementioned molding step.

In the molding step, for example, a sheet-shaped material is fed out from two material rolls on which there are wound, respectively, sheet materials that serve as the materials for the first sheet 40a and the second sheet 40b, and the assembly components (the filter member 64, the port members 44, 46) are supplied together therewith to a joining device such as a high-frequency fusion bonding device or the like. The joining device is equipped with upper and lower molds, and by carrying out blow molding while the two sheet-shaped materials are joined together with the assembly components, the cassette 28 is molded with the flow path 42 formed therein. In this case, the tubes 32, 34 may be connected at the time that the cassette 28 is molded in the joining device.

In the sterilization step, for example, autoclave sterilization is performed on the cassette 28 that was obtained by the molding step. Since the cassette 28 is made of a material which can withstand the heat of autoclave sterilization, the cassette 28 will not be melted when subjected to heat of sterilization. Further, since the cassette 28 is made of a material that is permeable to water vapor, water vapor, which is a treatment gas employed in autoclave sterilization, is introduced into the flow path 42 of the cassette 28. Accordingly, the cassette 28 can be suitably sterilized. EOG sterilization may also be performed in the sterilization step.

In the sterilization step, the entirety of the blood collection circuit set 12 including the plurality of bags 24 (the ACD solution bag 24a, etc.) may be sterilized. Consequently, the blood collection circuit set 12 can be sterilized efficiently.

In FIG. 1, the centrifugal separation device 14 is a device that is used repeatedly in blood component collection, and is provided, for example, in a medical facility, a blood collection vehicle, or the like. The centrifugal separation device 14 is equipped with the centrifuge unit 18 having the rotor 18a, and a cassette mounting unit 84 having a cassette holder 86 that is configured in a manner to retain the cassette 28 of the blood collection circuit set 12.

Figure 6:
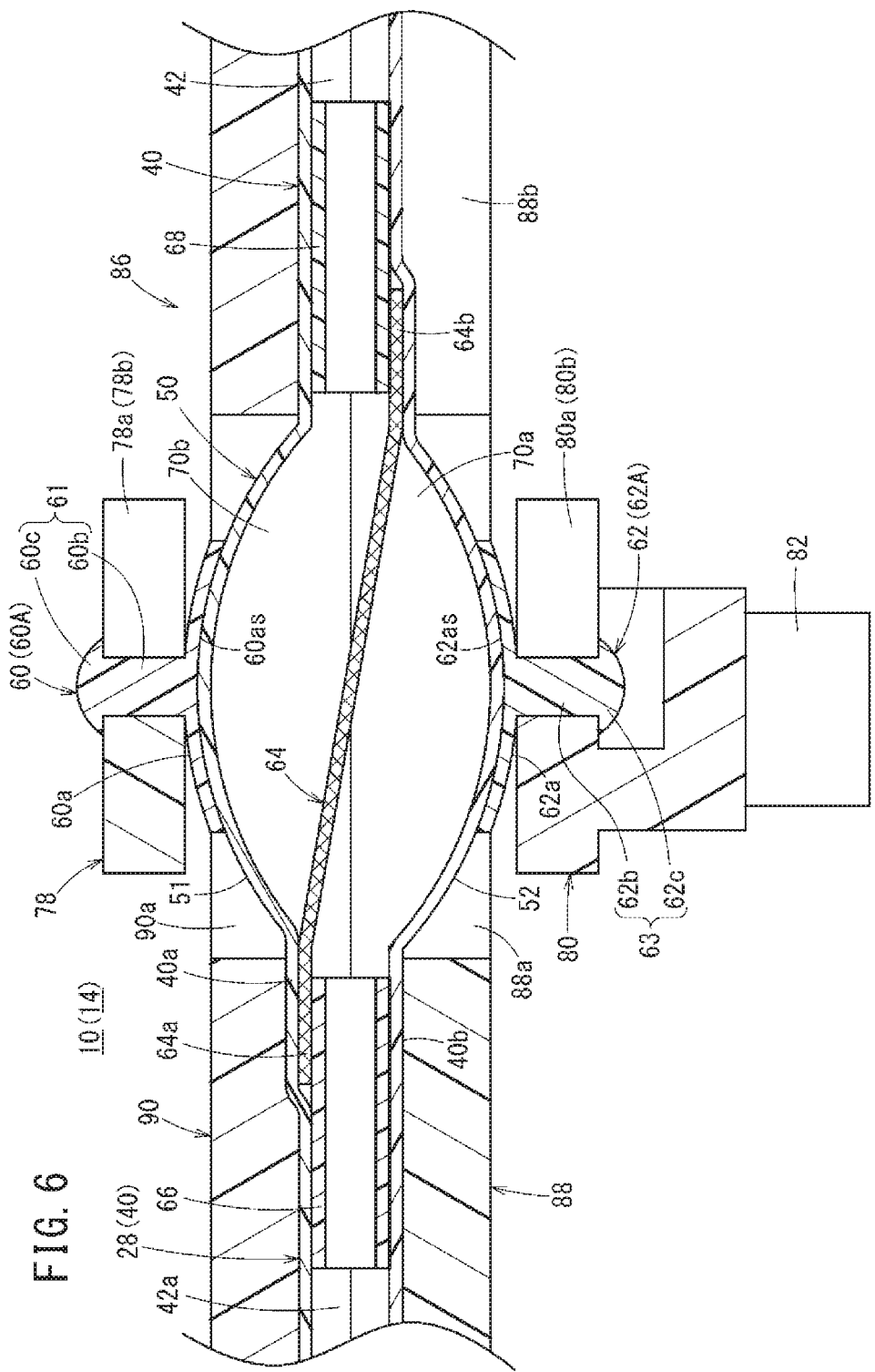
FIG. 6 is a cross-sectional view showing a state in which the blood component collection cassette is mounted in the cassette holder.

As shown in FIG. 6, the centrifugal separation device 14 includes a first gripping member 78 which is capable of gripping the first gripped member 60 of the cassette 28, a second gripping member 80 which is capable of gripping the second gripped member 62 of the cassette 28, and a load detection unit 82 to which the second gripping member 80 is fixed. The load detection unit 82 is constituted, for example, by a load cell.

The first gripping member 78 has a first engagement groove 78a which is capable of engaging with the first gripped member 60. The first engagement groove 78a is shaped in the form of an engagement slit 78b (refer also to FIG. 5) into which the shaft portion 60b of the first engagement member 60A can be inserted. In the case that an engagement groove is provided on the first gripped member 60 instead of the engagement protrusion 61, an engagement protrusion which is capable of engaging with the engagement groove is provided on the first gripping member 78.

The second gripping member 80 is arranged face-to-face with the first gripping member 78. The second gripping member 80 has a second engagement groove 80a which is capable of engaging with the second gripped member 62. The second engagement groove 80a is shaped in the form of an engagement slit 80b into which the shaft portion 62b of the second engagement member 62A can be inserted. In the case that an engagement groove is provided on the second gripped member 62 instead of the engagement protrusion 63, an engagement protrusion which is capable of engaging with the engagement groove is provided on the second gripping member 80. The second engagement groove 80a opens in the same direction as the first engagement groove 78a.

As the constituent material of the first gripping member 78 and the second gripping member 80, there may be cited, for example, vinyl chloride, cyclic polyolefin, polypropylene, polycarbonate, and the like. The first gripping member 78 and the second gripping member 80 may also be made from a metal material.

Figure 5:
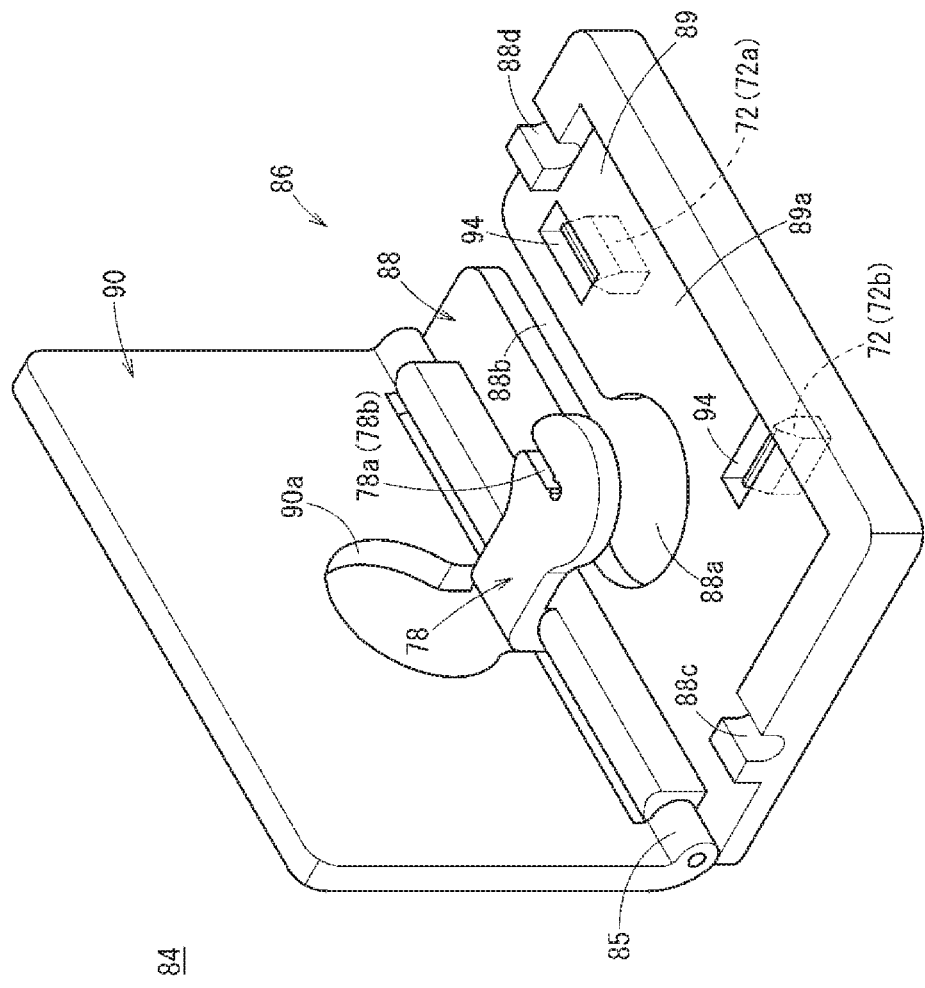
FIG. 5 is a perspective view of a cassette holder.

As shown in FIG. 5, the cassette holder 86 includes an attachment base 88 in which there is provided a cassette mounting groove 89 having a shape corresponding to the outer peripheral shape of the cassette body 40, and a lid 90 which is capable of being opened and closed with respect to the attachment base 88. The attachment base 88 and the lid 90 are constituted from a hard material. The first gripping member 78 is disposed at a position which is fixed with respect to the attachment base 88. The first gripping member 78 may be formed integrally with the attachment base 88, or may be a separate member that is fixed to the attachment base 88.

The attachment base 88 includes an opening 88a therein which is capable of receiving at least a part of the second bulging portion for pressure measurement 52, and a slit 88b that communicates with the opening 88a together with allowing passage of the second gripped member 62 therethrough. The opening 88a and the slit 88b penetrate in the thickness direction of the attachment base 88. A first port arrangement groove 88c into which the first port member 44 of the cassette 28 can be arranged, and a second port arrangement groove 88d into which the second port member 46 of the cassette 28 can be arranged are provided on the outer peripheral portion of the attachment base 88. The first port arrangement groove 88c and the second port arrangement groove 88d are in communication with the cassette mounting groove 89.

The lid 90 is connected in a rotatable manner to the attachment base 88 via a hinge 85. When the lid 90 is closed with the cassette 28 being held in the cassette mounting groove 89 of the attachment base 88, the cassette 28 is sandwiched between the attachment base 88 and the lid 90. An opening 90a, which is capable of receiving at least a part of the first bulging portion for pressure measurement 51, is provided in the lid 90. By providing the opening 90a, it is possible to prevent the lid 90 from interfering with the first gripping member 78 when the lid 90 is closed. Further, since the opening 88a is provided in the attachment base 88 together with the opening 90a that is provided in the lid 90, the cassette 28 can suitably be retained between the attachment base 88 and the lid 90, while squeezing of the bulging structure 50 is prevented.

The cassette mounting unit 84 further includes the plurality of clamps 72 (72a, 72b) configured to be capable of pressing the clamp action members 76 of the cassette 28. The plural clamps 72 are capable of being advanced and retracted in the cassette thickness direction in a state in which a cassette is held in the cassette mounting groove 89, and are disposed corresponding to the arrangement of the plurality of clamp action members 76 (76a, 76b) provided on the cassette 28. The plural clamps 72 are capable of pressing the plurality of clamp action members 76, respectively, via a plurality of holes 94 that open on a bottom surface 89a of the cassette mounting groove 89.

At a time that the clamp action members 76 are not being pressed by the clamps 72, in a state in which the cassette 28 is mounted in the cassette mounting unit 84, the flow paths inside the clamp action members 76 are opened. When the clamps 72 protrude from the holes 94 and press the clamp action members 76, the flow paths inside the clamp action members 76 are closed. In addition, when the clamps 72 are retracted, due to the elastic restorative force of (the clamp action members 76 of) the cassette body 40, the clamp action members 76 are restored to their original shape, and the flow paths inside the clamp action members 76 are opened.

As shown in FIG. 1, the centrifugal separation device 14 includes an ACD solution transfer pump 98 which acts on the ACD solution transfer tube 23, and a blood collection and blood returning pump 100 which acts on the treatment unit side tube 34 that is connected to the cassette 28. The ACD solution transfer pump 98 is a pump that transfers the ACD solution from the ACD solution bag 24a to the cassette 28 and the blood treatment unit 16 via the ACD solution transfer tube 23. The blood collection and blood returning pump 100 is a pump that transfers blood from the blood donor to the blood treatment unit 16, and together therewith, transfers blood from the blood treatment unit 16 back to the blood donor. The ACD solution transfer pump 98 and the blood collection and blood returning pump 100 are constituted, for example, by a roller pump or a finger pump.

The centrifugal separation device 14 further includes a control unit 102 adapted to control the centrifuge unit 18, the cassette mounting unit 84, and the pumps 98, 100. The operations of the aforementioned plurality of clamps 72 are controlled by the control unit 102. The control unit 102 includes a computation unit 103 which, when the centrifugal separation device 14 is in operation, acquires (calculates) the circuit internal pressure (circuit internal pressure of the cassette 28) of the blood collection circuit set 12, on the basis of the load detected by the load detection unit 82 (see FIG. 6).

Next, operations of the blood component collection system 10 according to the present embodiment, which is configured in the manner described above, will be described in relation to a flow path internal pressure detection method according to the present embodiment.

As a preparation (set-up) for collecting blood components from a blood donor using the blood component collection system 10 shown in FIG. 1, the blood collection circuit set 12 is attached to the centrifugal separation device 14. More specifically, the cassette 28 is mounted in the cassette mounting unit 84, and the blood treatment unit 16 is attached to the rotor 18a. On the other hand, the blood collecting needle 20 pierces and is inserted into the blood donor.

Figure 7:
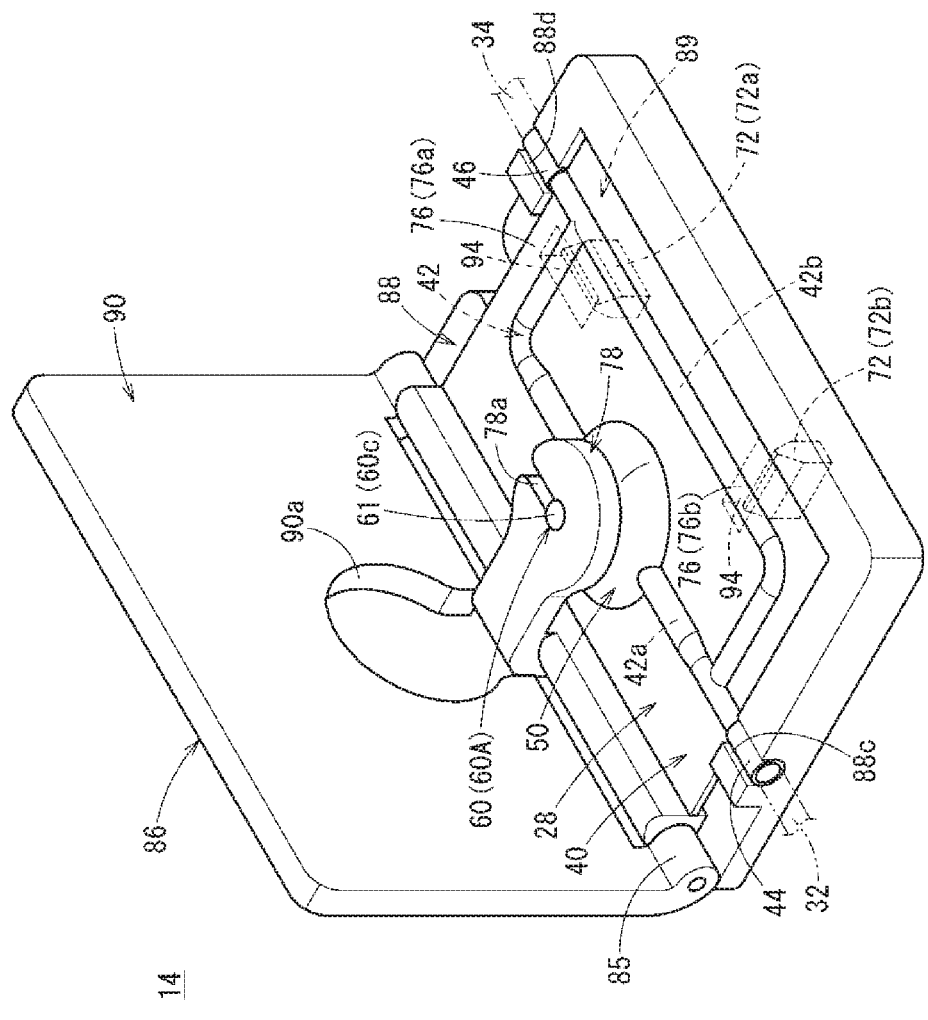
FIG. 7 is a perspective view showing a state in which the blood component collection cassette is mounted in the cassette holder.

When the cassette 28 is mounted in the cassette mounting unit 84, as shown in FIG. 7, the cassette body 40 is fitted into the cassette mounting groove 89. Next, the first port member 44 and the second port member 46 are inserted respectively into the first port arrangement groove 88c and the second port arrangement groove 88d. In addition, by closing the lid 90, the cassette 28 is sandwiched and held between the lid 90 and the attachment base 88.

As a result, a state is brought about in which the plural clamp action members 76 of the cassette 28 are placed face-to-face with the plurality of clamps 72. Further, as shown in FIG. 6, the first gripped member 60 of the cassette 28 is gripped by the first gripping member 78. In this case, accompanying the engagement protrusion 61 being inserted into the first engagement groove 78a, the first gripping member 78 is sandwiched between the fixed base 60a and the engagement claw 60c. Further, the second gripped member 62 is gripped by the second gripping member 80. In this case, accompanying the engagement protrusion 63 being inserted into the second engagement groove 80a, the second gripping member 80 is sandwiched between the fixed base 62a and the engagement claw 62c. In a state in which the first gripped member 60 is gripped by the first gripping member 78, the first gripped member 60 is prevented from moving relatively (rattling) in the cassette thickness direction with respect to the first gripping member 78. In a state in which the second gripped member 62 is gripped by the second gripping member 80, the second gripped member 62 is prevented from moving relatively (rattling) in the cassette thickness direction with respect to the second gripping member 80.

In this manner, the flow path internal pressure detection method includes a gripping step, in which the first gripped member 60, which is provided on one surface in the thickness direction of the bulging structure 50, is gripped by the first gripping member 78 provided on the centrifugal separation device 14, and together therewith, the second gripped member 62, which is provided on the other surface in the thickness direction of the bulging structure 50, is gripped by the second gripping member 80 provided on the centrifugal separation device 14.

When a command is issued by operation of a user with respect to the centrifugal separation device 14 as shown in FIG. 1 in order to initiate operations, in the centrifugal separation device 14, under the action of the ACD solution transfer pump 98, priming with the ACD solution is carried out. More specifically, in the priming, the ACD solution is introduced from the ACD solution bag 24a into the flow path 42 inside the cassette 28 via the ACD solution transfer tube 23, and at a stage at which it is detected by a non-illustrated line sensor disposed on the flow path 42 (or externally of the cassette 28) that the ACD solution has come into close proximity to the first line 42a, priming by the ACD solution is completed.

Next, by rotating the rotor 18a, the centrifugal separation device 14 applies a centrifugal force to the blood treatment unit 16 that is attached to the rotor 18a, and together therewith, by operation of the blood collection and blood returning pump 100, blood (whole blood) from the blood donor is extracted and introduced into the blood treatment unit 16 (blood collection operation). By the centrifugal force that accompanies rotation of the rotor 18a, the blood introduced into the blood treatment unit 16 is separated into red blood cells (concentrated red blood cells), a buffy coat, and plasma (platelet-poor plasma).

The plasma that is obtained by separation in the blood treatment unit 16 is introduced into the PPP bag 24b via the PPP transfer tube 36. After completion of the centrifugal separation process, the remaining blood components (the red blood cells and the buffy coat) are returned to the blood donor (blood returning operation). At this time, since blood clumps (clotted blood) contained within the remaining blood components are trapped by the filter member 64 provided in the cassette 28, any risk of clotted blood being returned to the donor can be reduced. The above-described blood collection operation and blood returning operation are repeated a plurality of times.

The flow path internal pressure detection method further includes a measurement step and an internal pressure calculating step. In the measurement step, in a state in which the first gripped member 60 is gripped by the first gripping member 78, the second gripped member 62 is gripped by the second gripping member 80, and blood is being delivered to the bulging structure 50, the load acting on the load detection unit 82 that is fixed to the second gripping member 80 is measured. In the internal pressure calculating step, the internal pressure of the flow path 42 is calculated on the basis of the load measured by the load detection unit 82.

During operation of the blood component collection system 10, the clamps 72 (see FIG. 5) of the centrifugal separation device 14 are operated in the following manner.

Figure 8:
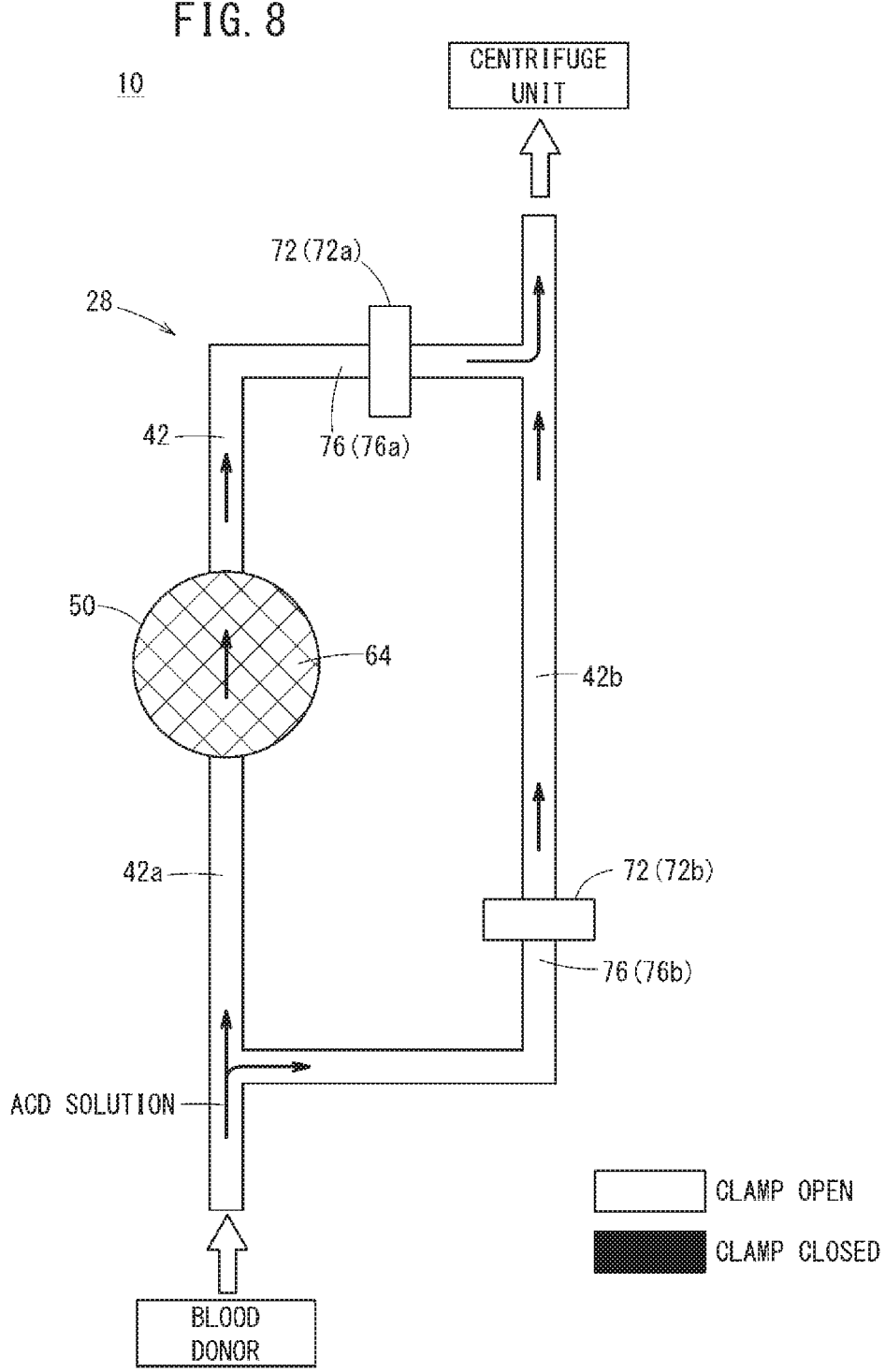
FIG. 8 is a first explanatory diagram illustrating the operation of clamps.

As shown in FIG. 8, when priming is carried out by the ACD solution, the clamps 72a, 72b are opened. In addition, in this state, the ACD solution is introduced into the flow path 42 in the immediate vicinity of the first line 42a of the cassette 28, and at a stage at which it is detected by the non-illustrated line sensor disposed on the flow path 42 (or externally of the cassette 28) that the ACD solution has come into close proximity to the first line 42a, priming by the ACD solution is completed.

Figure 9:
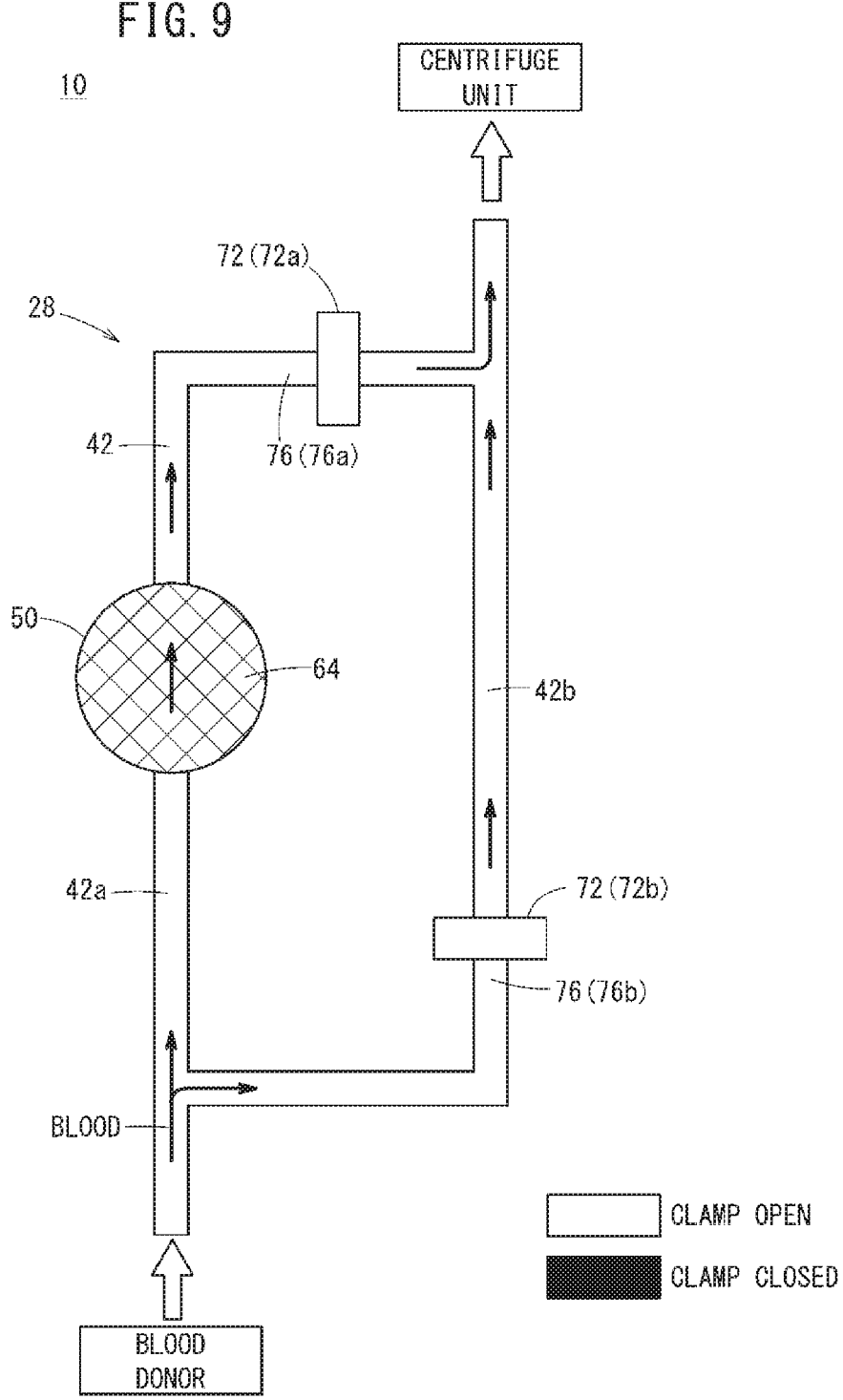
FIG. 9 is a second explanatory diagram illustrating operation of the clamps.

Next, when blood collection is performed for the first time, as shown in FIG. 9, the state in which the clamps 72a, 72b are opened is maintained. In addition, in this state, blood from the blood donor is introduced into the flow path 42 of the cassette 28, and all of the air inside the cassette 28 is pushed out by the blood into the blood treatment unit 16.

Figure 10:
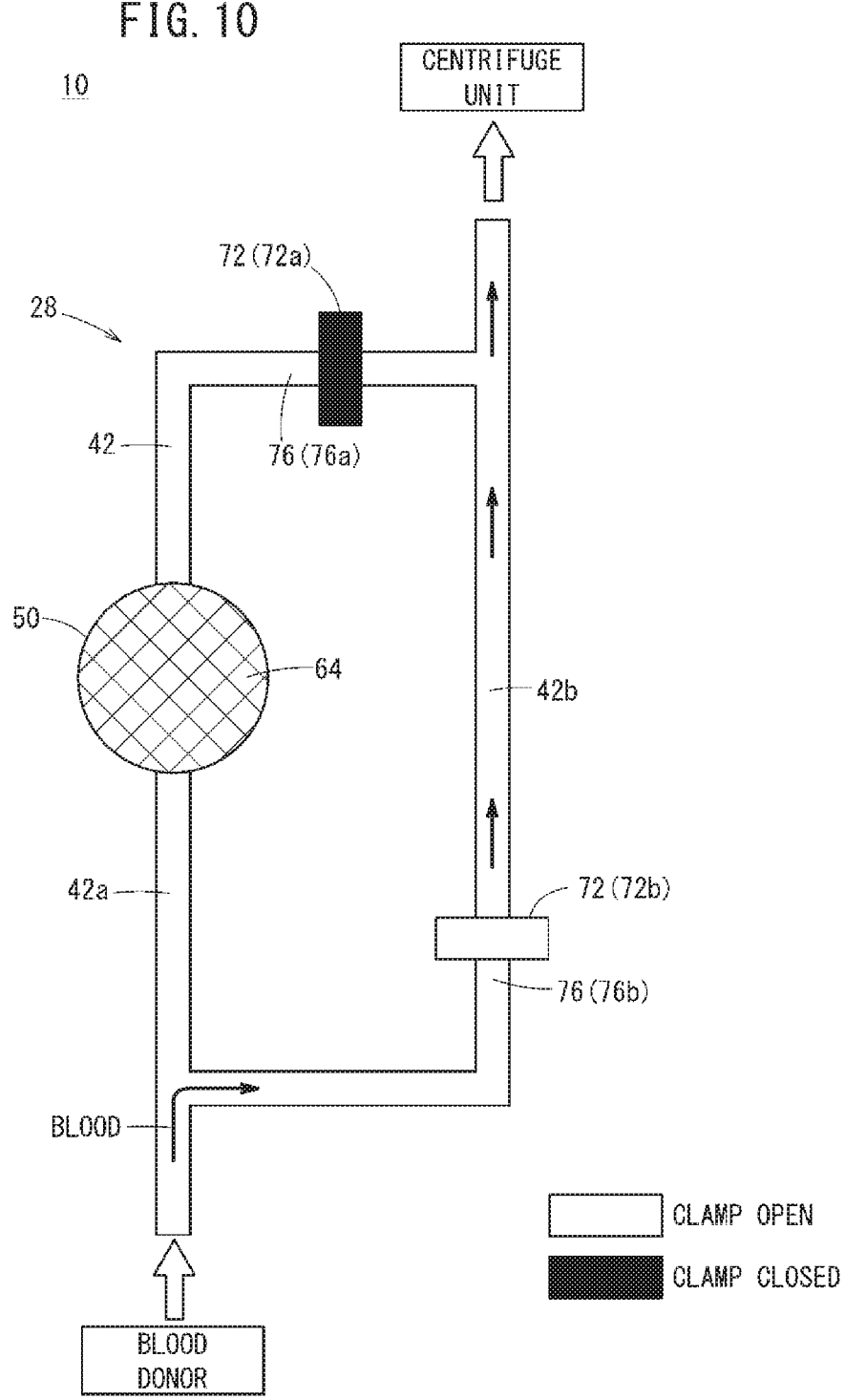
FIG. 10 is a third explanatory diagram illustrating operation of the clamps.

During the course of the initial blood collection, as shown in FIG. 10, the clamp 72a is closed while the opened state of the clamp 72b is maintained, and thereby, the first line 42a is closed. Consequently, a negative pressure is prevented from acting on the bulging structure 50, and blockage of the bulging structure 50 (filter chamber) is prevented.

Figure 11:
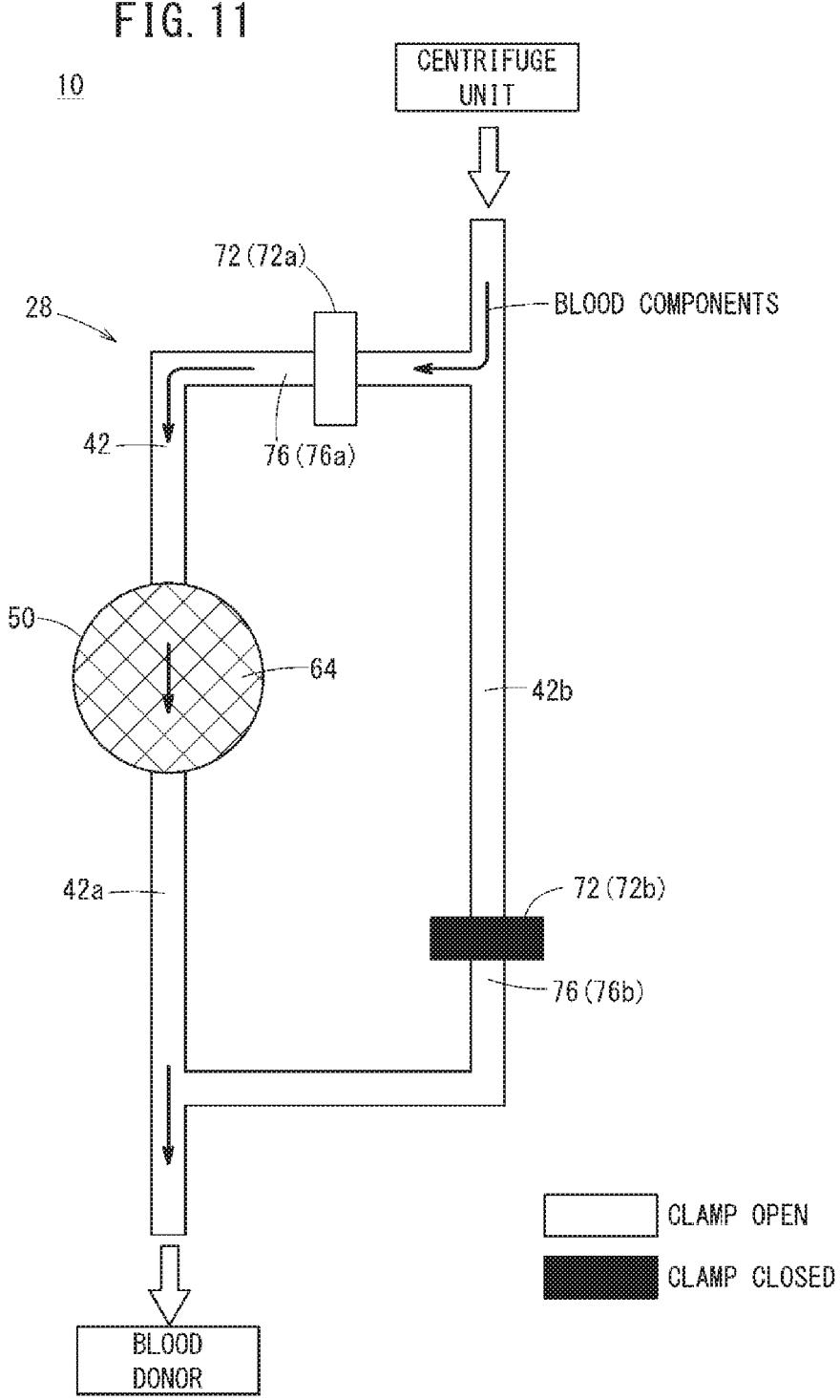
FIG. 11 is a fourth explanatory diagram illustrating operation of the clamps.

Next, when return of the blood components to the blood donor is carried out, as shown in FIG. 11, the clamp 72b is closed and the clamp 72a is opened. Thus, the second line 42b is closed, whereas the first line 42a is opened. Accordingly, when the blood components pass through the filter member 64, clotted blood contained within the blood components is trapped in the filter member 64. Since the first line 42a is closed, clotted blood cannot be returned to the donor via the second line 42b.

Figure 12:
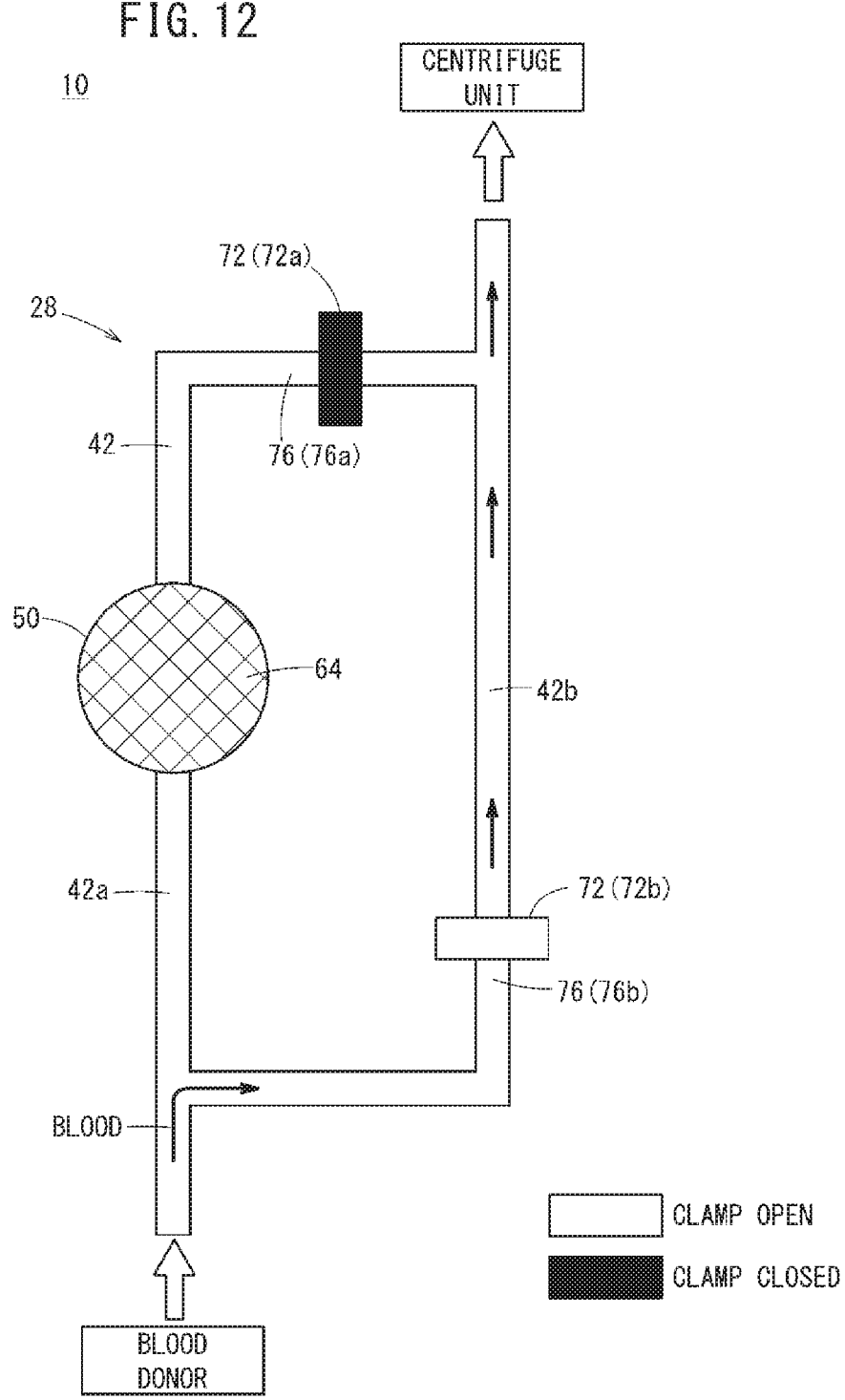
FIG. 12 is a fifth explanatory diagram illustrating operation of the clamps.

Next, when second and subsequent blood collections are carried out, as shown in FIG. 12, the clamp 72a is closed and the clamp 72b is opened. Thus, the first line 42a is closed, whereas the second line 42b is opened. Accordingly, from among the first line 42a and the second line 42b, blood is transferred or delivered via only the second line 42b to (the centrifuge unit 18 of) the blood treatment unit 16. Thereafter, return of the blood (see FIG. 11) is carried out again. Collection of blood and return of the blood in this manner are repeated a plurality of times.

When the final return of blood is performed, the clamp 72b is closed and the clamp 72a is opened, as shown in FIG.

11, in order to return blood components in as large an amount as possible to the blood donor.

In this case, the cassette 28, the blood component collection system 10, and the flow path internal pressure detection method according to the present embodiment exhibit the following effects.

As examples of the sterilization process used at the time of manufacturing the cassette 28 shown in FIG. 2, etc., there may be cited EOG sterilization, autoclave sterilization, and the like. Further, since the cassette body 40 can be obtained by fusion bonding the first sheet 40a and the second sheet 40b which are made of a soft material, the cassette can be manufactured at a lower cost, as compared with a conventional cassette made of a hard resin and which is manufactured by injection molding.

In accordance with the blood component collection system 10, it is possible to accurately measure the circuit internal pressure (negative pressure and positive pressure) by the load detection unit 82 which is provided on the centrifugal separation device 14, without applying an initial reaction force for pressure measurement to the cassette body 40. More specifically, as shown in FIG. 6, the first gripped member 60 provided on the first bulging portion for pressure measurement 51 is gripped by the first gripping member 78 that is provided on the centrifugal separation device 14, and the second gripped member 62 provided on the second bulging portion for pressure measurement 52 is gripped by the second gripping member 80 that is provided on the centrifugal separation device 14. Therefore, the circuit internal pressure acts on the load detection unit 82 that is fixed to the second gripping member 80. More specifically, in the case that the circuit internal pressure is a positive pressure, a pressing load acts on the load detection unit 82 via the second gripping member 80. On the other hand, in the case that the circuit internal pressure is a negative pressure, a tensile load is applied on the load detection unit 82 via the second gripping member 80. Accordingly, the circuit internal pressure can be measured on the basis of the load detected by the load detection unit 82. In this case, the control unit 102 (see FIG. 1) of the centrifugal separation device 14 has stored therein a calibration curve (calibration curve data) showing a relationship between the load and the circuit internal pressure, and using the obtained load and the calibration curve data, it is possible to calculate the circuit internal pressure.

Incidentally, unlike the present embodiment, in the case of a method in which loads are detected under a condition in which the load detecting unit is pressed (an initial reaction force is imparted) to the cassette in order to measure the internal circuit pressure, and the pressed portion of the cassette is elastically deformed, since creeping occurs in the pressed portion as the pressed state is continued, the reaction force (the restorative force accompanying elastic deformation) from the cassette decreases over time. Such a decrease in the reaction force over time is a factor that lowers measurement accuracy. In contrast thereto, according to the present embodiment, by gripping the bulging structure 50 from both sides, the circuit internal pressure is measured without applying an initial reaction force that is a possible cause of such a measurement error. Consequently, it is possible to accurately measure the circuit internal pressure in both a negative pressure region and a positive pressure region.

Further, since the reaction force is relatively large in a low pressure region as compared with a high pressure region, in the case of a method in which an initial reaction force is applied, the adverse influence on the measurement error tends to be larger. In contrast thereto, in accordance with the blood component collection system 10, since the circuit internal pressure is measured while excluding the initial reaction force which can result in measurement errors, it is possible to highly accurately measure the circuit internal pressure.

According to the present embodiment, the first gripped member 60 is a first engagement member 60A which is fixed to the first bulging portion for pressure measurement 51 and which includes the engagement protrusion 61 or an engagement groove capable of engaging with the first gripping member 78. The second gripped member 62 is a second engagement member 62A which is fixed to the second bulging portion for pressure measurement 52 and which includes the engagement protrusion 63 or an engagement groove capable of engaging with the second gripping member 80. In accordance with this configuration, it is possible for the first gripped member 60 and the second gripped member 62 to be gripped respectively with a sufficient gripping force by the first gripping member 78 and the second gripping member 80, thus making it possible to stably measure the circuit internal pressure.

The cassette body 40 includes the flow path forming convex wall portion 58, which protrudes in the cassette thickness direction, together with forming in the interior thereof, from among the flow path 42, a flow path other than the flow path inside the bulging structure 50. In addition, the width W1 and the protruding height H1 of the bulging structure 50 from the plate-shaped base portion 41 is greater than the width W2 and protruding height H2 of the flow path forming convex wall portion 58 from the plate-shaped base portion 41 (see FIGS. 2 and 3). By this configuration, since the bulging structure 50 is easily deformed in accordance with the circuit internal pressure, the measurement accuracy of the circuit internal pressure can be improved.

The first bulging portion for pressure measurement 51 and the second bulging portion for pressure measurement 52 bulge in dome-shapes from the plate-shaped base portion 41. In accordance with this configuration, the manner in which deformation of the bulging structure 50 follows with respect to the circuit internal pressure is improved, and thus the measurement accuracy of the circuit internal pressure can be further improved. For this reason, it is possible to enhance the ability to transmit force to the load detection unit 82.

The first bulging portion for pressure measurement 51 and the second bulging portion for pressure measurement 52 are formed in a circular shape when viewed from the cassette thickness direction. In accordance with this configuration, it is possible to further improve the manner in which deformation of the bulging structure 50 follows with respect to the circuit internal pressure.

The first gripped member 60 is disposed on a central part of the first bulging portion for pressure measurement 51, and the second gripped member 62 is disposed on a central part of the second bulging portion for pressure measurement 52. In accordance with this configuration, it is possible to further improve the measurement accuracy of the circuit internal pressure.

As shown in FIG. 2, the flow path 42 includes the first line 42a in which the filter member 64 that serves to trap clotted blood is arranged, and the second line 42b in which the filter member 64 is not arranged. In addition, the filter member 64 is arranged inside the bulging structure 50. In accordance with this configuration, since the bulging structure 50 also serves to provide a filter function, the filter member 64 can be arranged in the cassette 28 without adding complexity to the flow path structure.

As shown in FIG. 7, the centrifugal separation device 14 is equipped with the cassette holder 86 that is capable of retaining the cassette 28, and the cassette holder 86 includes the attachment base 88 in which there is provided the cassette mounting groove 89 having a shape corresponding to the outer peripheral shape of the cassette body 40, and the lid 90 which is capable of being opened and closed with respect to the attachment base 88. In accordance with this configuration, it is possible to easily attach the cassette 28 to a predetermined position of the centrifugal separation device 14, thereby improving workability when attaching the cassette 28.

The first gripping member 78 is disposed at a position fixed with respect to the attachment base 88, and the second gripping member 80 is arranged face-to-face with the first gripping member 78. In accordance with this configuration, accompanying attachment of the cassette 28 to the cassette mounting groove 89, the first gripped member 60 is gripped by the first gripping member 78, together with the second gripped member 62 being gripped by the second gripping member 80, and therefore, workability when attaching the cassette 28 can be further improved.

As shown in FIG. 5, the attachment base 88 includes the opening 88a therein which is capable of receiving at least a part of the second bulging portion for pressure measurement 52, and the slit 88b that communicates with the opening 88a together with allowing passage of the second gripped member 62 therethrough. In accordance with this configuration, it is possible to further simplify the attachment of the cassette 28 to the cassette mounting groove 89.

Figure 13:
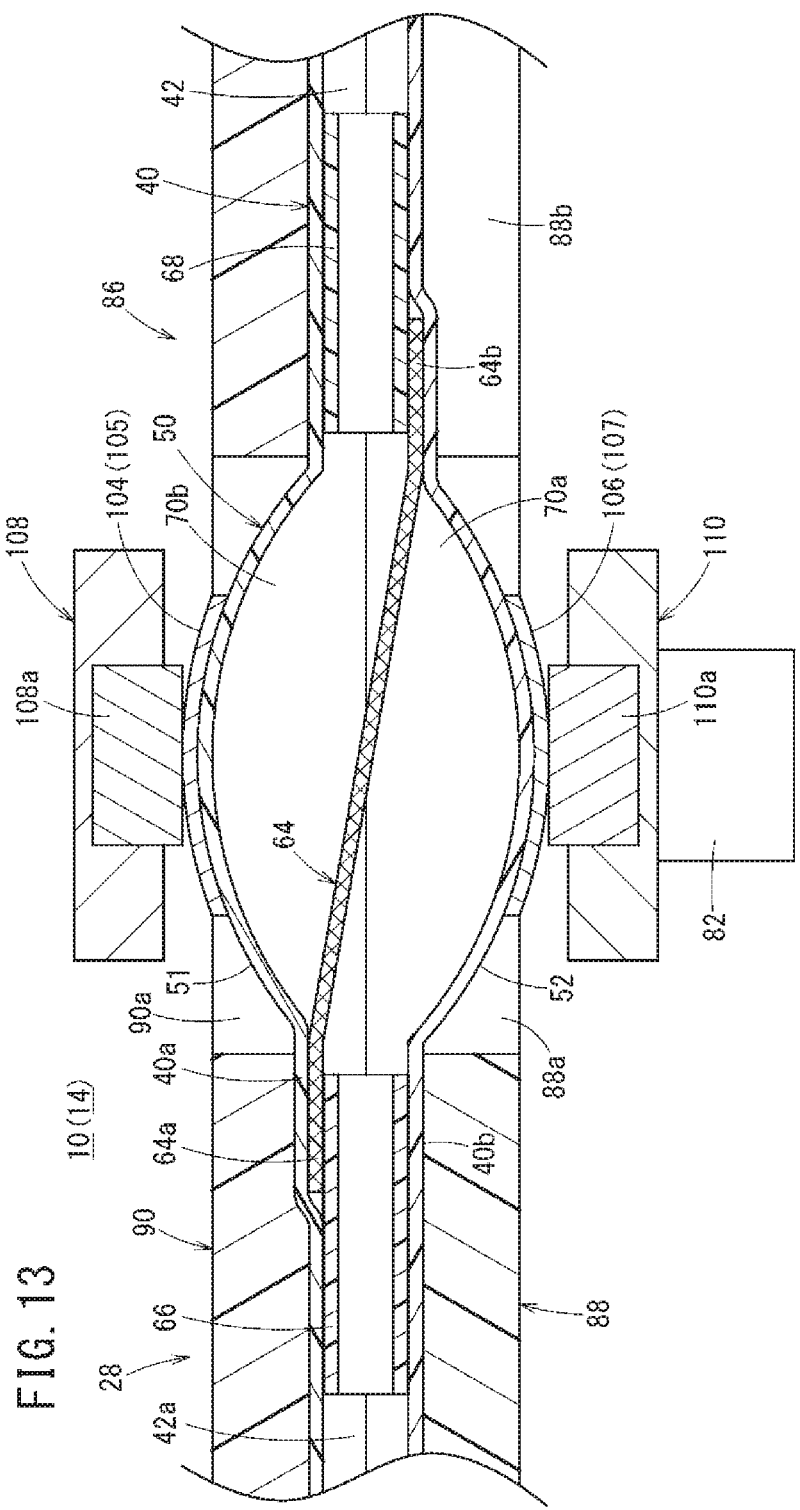
FIG. 13 is a view showing a modified example of the blood component collection system.

As shown in FIG. 13, a first gripped member 105 which is made up from a first magnet 104 may be provided on the first bulging portion for pressure measurement 51, and a second gripped member 107 which is made up from a second magnet 106 may be provided on the second bulging portion for pressure measurement 52, and the centrifugal separation device 14 may be equipped with a first gripping member 108 having a first gripping magnet 108a, and a second gripping member 110 having a second gripping magnet 110a and to which the load detection unit 82 is fixed. By attracting the first magnet 104 with a magnetic force, the first gripping member 108 is capable of gripping the first bulging portion for pressure measurement 51 via the first magnet 104. Further, by attracting the second magnet 106 with a magnetic force, the second gripping member 110 is capable of gripping the second bulging portion for pressure measurement 52 via the second magnet 106.

The first magnet 104 and the second magnet 106, for example, are magnetic coating layers formed on respective surfaces of the first bulging portion for pressure measurement 51 and the second bulging portion for pressure measurement 52. The first magnet 104 and the second magnet 106 may also be in the form of magnetic plates which are fixed to the respective surfaces of the first bulging portion for pressure measurement 51 and the second bulging portion for pressure measurement 52. The first magnet 104 and the second magnet 106 may also be inserted (or laminated) onto the respective sheets that make up the first bulging portion for pressure measurement 51 and the second bulging portion for pressure measurement 52. Similar to the above-described first gripping member 78 (see FIG. 5), the first gripping member 108 may be a portion that is formed integrally with the attachment base 88, or may be a member that is fixed to the attachment base 88. The first gripping member 108 may be a portion formed integrally with the lid 90, or may be a member that is fixed to the lid 90.

Figure 14:
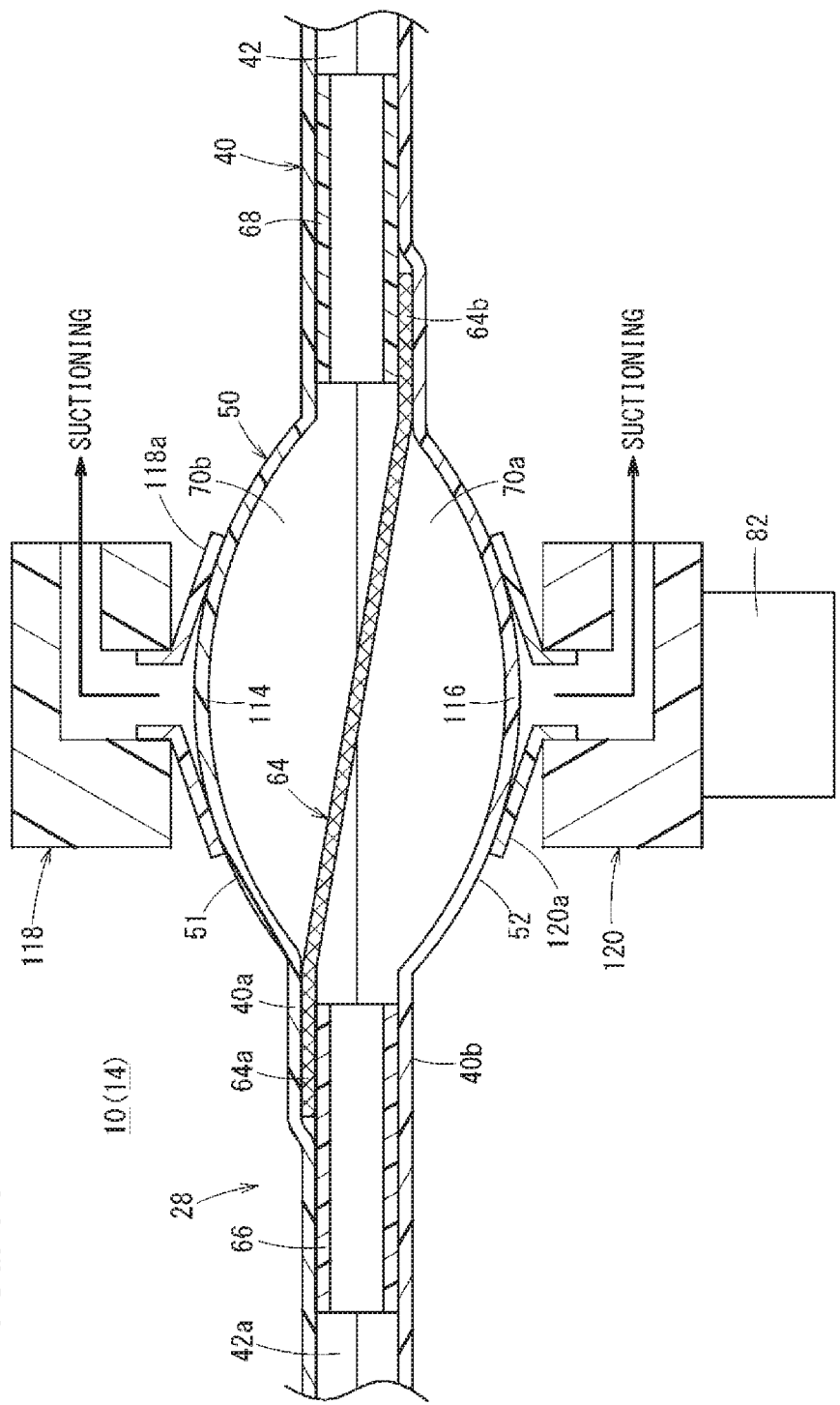
FIG. 14 is a diagram showing another modified example of the blood component collection system.

As shown in FIG. 14, the first gripped member 114 may be provided as a portion of the first bulging portion for pressure measurement 51 itself, and the second gripped member 116 may be provided as a portion of the second bulging portion for pressure measurement 52 itself, and the centrifugal separation device 14 may be equipped with a first gripping member 118 having a first suction cup 118a, and a second gripping member 120 to which the load detection unit 82 is fixed and which has a second suction cup 120a. The first gripping member 118 is capable of directly gripping the first bulging portion for pressure measurement 51 by vacuum suctioning the internal flow path of the first suction cup 118a. The second gripping member 120 is capable of directly gripping the second bulging portion for pressure measurement 52 by vacuum suctioning the internal flow path of the second suction cup 120a.

In the above-described cassette 28, the flow path 42 is formed between the first sheet 40a and the second sheet 40b, which are formed of a soft material, however, the structure that forms the flow path 42 is not necessarily limited to such a configuration. For example, within the cassette body, apart from the internal flow path of the bulging structure 50, the members that form the flow path 42 may be tubes. In this case, the cassette body is equipped with two first tubes having a flow path constituting the first line 42a, and which are connected respectively to the first tube member 66 and the second tube member 68, and a second tube having a flow path constituting the second line 42b, and the cassette body further comprises a plate-shaped cassette base portion supporting the two first tubes and the second tube. The cassette base portion is constituted from a hard material.

The clamp action member 76a (see FIG. 2) is provided on one of the first tubes. The clamp action member 76b (see FIG. 2) is provided on the second tube. The cassette base portion is formed with the first gripped member and the second gripped member being exposed thereon, in a manner so that the first gripping member can grip the first gripped member, and the second gripping member is capable of pressing the second gripped member. Further, the cassette base portion is formed with the clamp action members 76a, 76b being exposed thereon, in a manner so that the clamps 72a, 72b can press on the clamp action members 76a, 76b.

Figure 15:
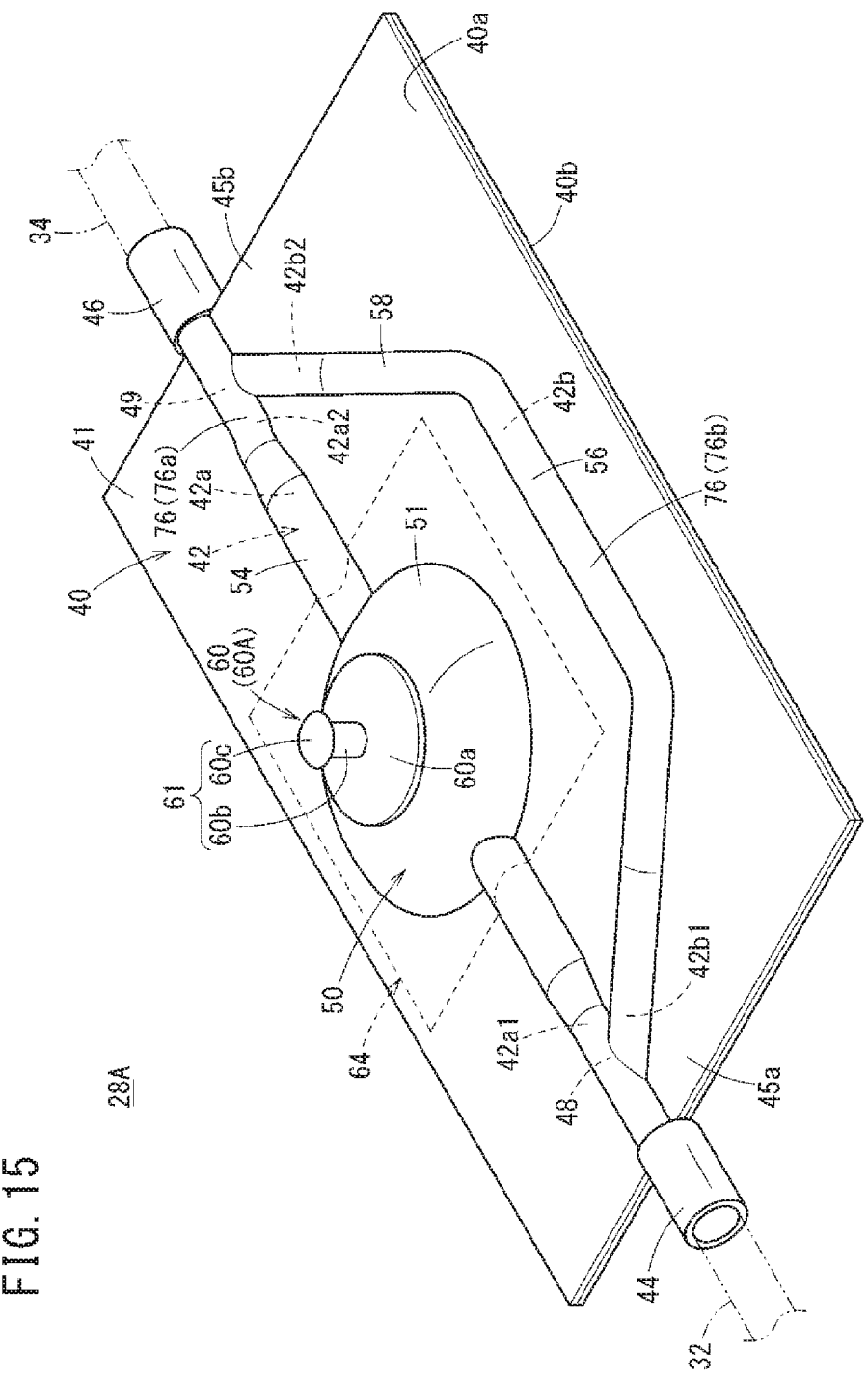
FIG. 15 is a perspective view of a blood component collection cassette according to another embodiment.

In the above-described blood component collection system 10, a blood component collection cassette 28A (hereinafter referred to as a "cassette 28A") shown in FIG. 15 may be adopted instead of the cassette 28. The flow path 42 includes the first line 42a in which a filter member 64 is arranged for removing clotted blood contained in the blood or the blood components, and the second line 42b in which the filter member 64 is not disposed. The one end side 42a1 of the first line 42a and the one end side 42b1 of the second line 42b are connected via a first branching member 48. The other end side 42a2 of the first line 42a and the other end side 42b2 of the second line 42b are connected via a second branching member 49. The first line 42a and the second line 42b extend at least partially in parallel with each other. The first branching member 48 and the second branching member 49 make up part of the flow path 42.

The rectangular cassette body 40 includes a first end portion 45a, which is one end part in the elongate axial direction, and a second end portion 45b, which is another end part in the elongate axial direction. The first port member 44 is provided at the first end portion 45a. The second port member 46 is provided at the second end portion 45b. The first port member 44 and the second port member 46 are arranged on the same straight line along the longitudinal axis of the cassette body 40.

The first branching member 48 is configured in a manner so that the change in the flow direction of the fluid at the first branching member 48 becomes an obtuse angle. More specifically, the one end side 42b1 of the second line 42b is connected to the first line 42a while being inclined toward the side of the second end portion 45b of the cassette body 40.

The second branching member 49 is configured in a manner so that the change in the flow direction of the fluid at the second branching member 49 becomes an obtuse angle. More specifically, the other end side 42b2 of the second line 42b is connected to the first line 42a while being inclined toward the side of the first end portion 45a of the cassette body 40.

In this manner, in accordance with the cassette 28A, the first branching member 48 and the second branching member 49 are configured in a manner so that the change in the flow direction of the fluid at the joint portions thereof becomes an obtuse angle. In accordance with such a configuration, it is possible to reduce damage to the blood when the blood flows through the respective joint portions.

Figure 16:
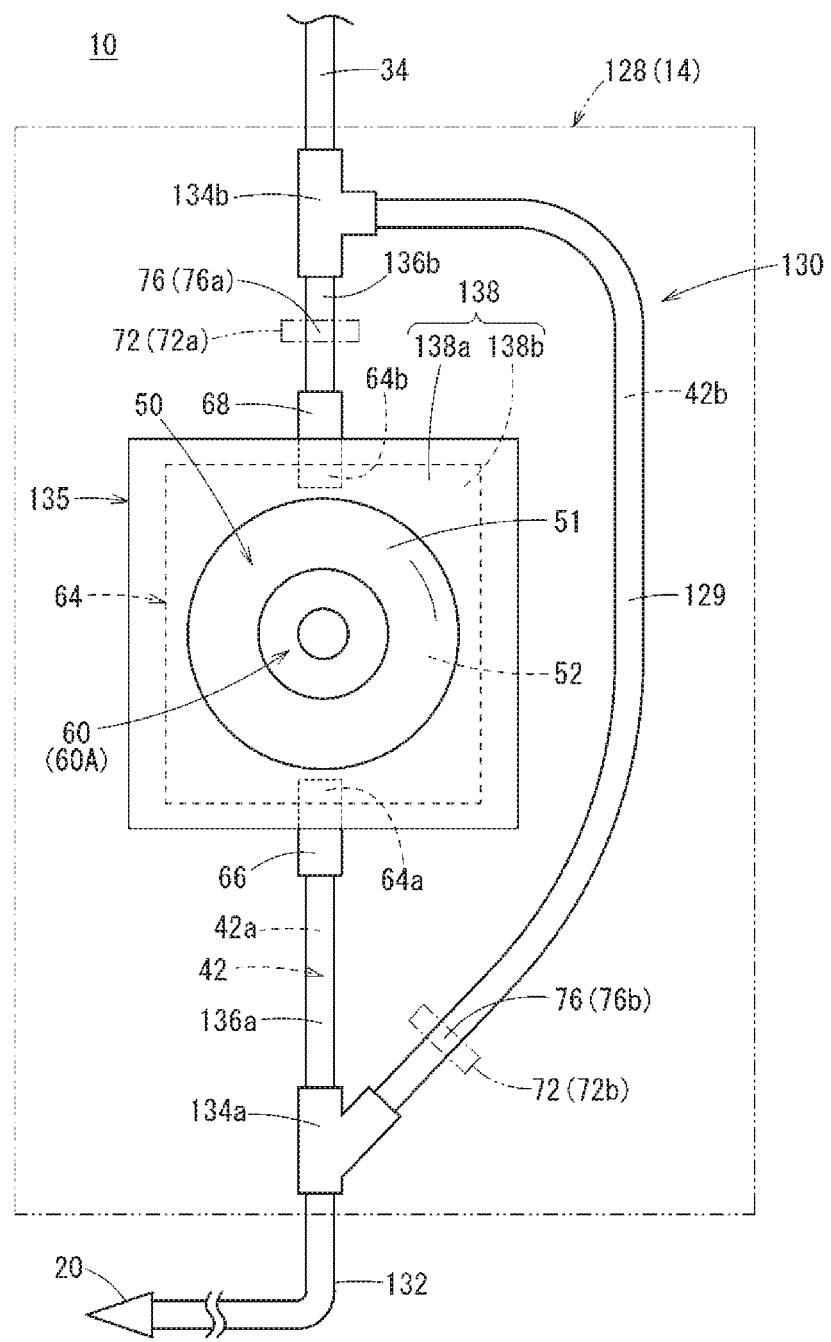
FIG. 16 is a schematic diagram of a blood component collection kit.

In the above-described blood component collection system 10, a blood component collection kit 130 (hereinafter referred to as a "kit 130") shown in FIG. 16 may be adopted instead of the cassette 28. In the kit 130, the same or equivalent constituent elements as those of the cassette 28 are denoted by the same reference numerals. In the kit 130, the majority of the members that form the flow path 42 in the cassette 28 are constituted by tubes.

More specifically, the kit 130 comprises a blood collecting needle 20 for collecting blood from a blood donor, a blood collecting tube 132 with one end thereof connected to the blood collecting needle 20, a first tube 136a with one end thereof connected to the blood collecting tube 132 via a first tube connector 134a, a cassette portion for pressure measurement 135 with one end thereof connected to the other end of the first tube 136a, and another first tube 136b with one end thereof connected to the other end of the cassette portion for pressure measurement 135. The flow paths in the two first tubes 136a, 136b and the flow path in the cassette portion for pressure measurement 135 constitute the first line 42a. The cassette portion for pressure measurement 135 is equipped with a cassette body 138 in which a first sheet 138a and a second sheet 138b, which are formed of a soft material, are stacked in the thickness direction and are joined to each other.

In the cassette body 138, a bulging structure 50 is provided having a first bulging portion for pressure measurement 51 and a second bulging portion for pressure measurement 52. A filter member 64 is disposed between the first sheet 138a and the second sheet 138b. The configuration by which the filter member 64 is arranged in the cassette body 138 is the same as the configuration by which the filter member 64 is arranged in the cassette body 40 (see FIG. 4). More specifically, the filter member 64 has one end side 64a disposed between the first sheet 138a and the first tube member 66, and another end side 64b disposed between the second sheet 138b and the second tube member 68.

The kit 130 further includes a second tube 129 (second line forming member) with one end thereof connected to the blood collecting tube 132 via the first tube connector 134a, and the other end thereof connected to the first tube 136b via a second tube connector 134b. The flow path in the second tube 129 constitutes the second line 42b.

The blood collecting tube 132, the two first tubes 136a, 136b, and the second tube 129 are formed from a soft material. One end of the treatment unit side tube 34 is connected to the second tube connector 134b. The other end of the treatment unit side tube 34 is connected to the blood treatment unit 16 (see FIG. 1).

In the kit 130, there are provided the plurality of clamp action members 76 (76a, 76b) on which the plurality of clamps 72 (72a, 72b) provided in the centrifugal separation device 14 act. Moreover, in the case that the kit 130 is used, in the centrifugal separation device 14, there is provided a kit mounting unit 128 instead of the cassette mounting unit 84 (see FIG. 1). Although a detailed description thereof is omitted, the kit mounting unit 128 includes an attachment base having a mounting groove in which the kit 130 can be mounted, and a lid which is capable of being opened and closed with respect to the attachment base, and is constituted in a manner so that, when the lid is closed, the kit 130 is sandwiched between the attachment base and the lid.

The plurality of clamps 72 (72a, 72b) are arranged so as to correspond to the arrangement of the plurality of clamp action members 76 (76a, 76b). When the kit 130 is installed in the centrifugal separation device 14, the clamp action members 76 abut against or are placed so as to be face-to-face with their corresponding clamps 72. The clamp 72a is capable of pressing the first tube 136b. The clamp 72a may also be disposed so as to be capable of pressing the first tube 136a. The clamp 72b is capable of pressing the second tube 129.

In the case of using the kit 130, which is constituted as described above, similar to the case of using the cassette 28 shown in FIG. 2, etc., the load detection unit 82 (see FIG. 6) which is provided on the centrifugal separation device 14 can accurately measure the circuit internal pressure (negative pressure and positive pressure), without applying an initial reaction force for pressure measurement to the cassette body 138.

The present invention is not limited to the above-described embodiments, and various modifications may be adopted within a range that does not depart from the scope of the present invention.

The invention claimed is:

1. A blood component collection cassette comprising:
a cassette body with a flow path formed therein, and which is configured to be installed in a blood component separating device having a load detection unit, wherein the cassette body comprises a bulging structure having a bulging portion for pressure measurement, the bulging portion for pressure measurement bulging in a cassette thickness direction on at least one surface of the cassette body in the cassette thickness direction; and
a filter arranged inside the bulging structure,
wherein the bulging structure is formed of a soft material,
wherein the bulging structure contains in an interior thereof at least a portion of the flow path,
wherein on one surface of the bulging structure in a thickness direction thereof, there is provided a first gripped member which is configured to be gripped by a first gripping member provided on the blood component separating device,
wherein on another surface of the bulging structure in the thickness direction thereof, there is provided a second gripped member which is configured to be gripped by a second gripping member to which the load detection unit is fixed,
wherein the flow path includes a first line in which the bulging structure is arranged and a second line in which the bulging structure is not arranged, wherein the second line is spaced apart from the first line on the cassette body and includes a portion that is parallel to the first line, wherein the first gripped member comprises a first base portion having a first curved surface over an entirety of the first base portion, wherein the first curved surface conforms to the one surface of the bulging structure, and wherein the second gripped member comprises a second base portion having a second curved surface over an entirety of the second base portion, wherein the second curved surface conforms to the another surface of the bulging structure.

2. The blood component collection cassette according to claim 1, further comprising:

a first tube; and a second tube, wherein the cassette body includes a first sheet and a second sheet which are formed of a soft material, the first sheet and the second sheet are stacked and are bonded to each other, and the flow path is formed between the first sheet and the second sheet, wherein a first end of the filter is sandwiched between the first sheet and the first tube, and wherein a second end of the filter is sandwiched between the second sheet and the second tube.

3. The blood component collection cassette according to claim 1, wherein:

the first gripped member is a first engagement member which is fixed to the one surface of the bulging structure, and which has an engagement protrusion or an engagement groove which is configured to engage with the first gripping member; and the second gripped member is a second engagement member which is fixed to the another surface of the bulging structure and which has an engagement protrusion or an engagement groove which is configured to engage with the second gripping member.

4. The blood component collection cassette according to claim 1, wherein:

the cassette body is formed therein with another portion of the flow path other than the portion of the flow path contained within the bulging structure, and includes a flow path forming convex wall portion that protrudes in the cassette thickness direction; and a protruding height of the bulging structure from a plate-shaped base portion of the cassette body is greater than a protruding height of the flow path forming convex wall portion from the plate-shaped base portion, and a width of the bulging structure is greater than a width of the flow path forming convex wall portion.

5. The blood component collection cassette according to claim 1, wherein the bulging portion for pressure measurement bulges in a dome shape from the plate-shaped base portion, and wherein the second line branches from the first line on the cassette body at a first side of the bulging structure and at a second side of the bulging structure opposite the first side.

6. The blood component collection cassette according to claim 5, wherein the bulging portion for pressure measurement is formed in a circular shape as viewed in a plan view, and wherein the flow path is connected to a first port on a first edge of the cassette body that is at the first side of the bulging structure and to a second port on a second edge of the cassette body that is at the second side of the bulging structure.

7. The blood component collection cassette according to claim 1, wherein the first gripped member and the second gripped member are disposed on a central part of the bulging portion for pressure measurement.

8. The blood component collection cassette according to claim 1, wherein:

the one surface and the another surface of the bulging structure are convex surfaces over an entirety of the bulging structure, the cassette body comprises a first flat surface that transitions into the one surface and a second flat surface that transitions into the another surface, and the filter is configured to trap an agglutinated substance made up of blood components.

9. The blood component collection cassette according to claim 1, wherein the cassette body includes a flow path forming member configured to form the flow path and including the bulging structure therein, and a cassette base part made of a hard material and configured to support the flow path forming member.

10. The blood component collection cassette according to claim 3, wherein:

the cassette body is formed therein with another portion of the flow path other than the portion of the flow path contained within the bulging structure, and includes a flow path forming convex wall portion that protrudes in the cassette thickness direction; and a protruding height of the bulging structure from a plate-shaped base portion of the cassette body is greater than a protruding height of the flow path forming convex wall portion from the plate-shaped base portion, and a width of the bulging structure is greater than a width of the flow path forming convex wall portion.

11. The blood component collection cassette according to claim 6, wherein:

the cassette body is formed therein with another portion of the flow path other than the portion of the flow path contained within the bulging structure, and includes a flow path forming convex wall portion that protrudes in the cassette thickness direction; and a protruding height of the bulging structure from a plate-shaped base portion of the cassette body is greater than a protruding height of the flow path forming convex wall portion from the plate-shaped base portion.

12. A blood component collection system comprising:

a blood component separating device including a first gripping member, a second gripping member, and a load detection unit fixed to the second gripping member; and a blood component collection cassette configured to be installed in the blood component separating device, wherein the blood component collection cassette comprises a cassette body with a flow path formed therein, wherein the cassette body comprises a bulging structure having a bulging portion for pressure measurement, the bulging portion for pressure measurement bulging in a cassette thickness direction on at least one surface of the cassette body, wherein the bulging structure comprises a filter arranged therein, wherein the bulging structure is formed of a soft material, wherein the bulging structure contains in an interior thereof at least a portion of the flow path, wherein on one surface of the bulging structure in a thickness direction thereof, there is provided a first gripped member which is configured to be gripped by the first gripping member, wherein on another surface of the bulging structure in the thickness direction thereof, there is provided a second gripped member which is configured to be gripped by the second gripping member, wherein the blood component separating device acquires a pressure in an interior of the flow path, based on a load detected by the load detection unit, wherein the flow path includes a first line in which the bulging structure is arranged and a second line in which the bulging structure is not arranged, wherein the second line is spaced apart from the first line on the cassette body and includes a portion that is parallel to the first line, wherein the first gripped member comprises a first base portion having a first curved surface over an entirety of the first base portion, wherein the first curved surface conforms to the one surface of the bulging structure, wherein the second gripped member comprises a second base portion having a second curved surface over an entirety of the second base portion, and wherein the second curved surface conforms to the another surface of the bulging structure.

13. The blood component collection system according to claim 12, wherein the cassette body includes a first sheet and a second sheet which are formed of a soft material, the first sheet and the second sheet are stacked and are bonded to each other, and the flow path is formed between the first sheet and the second sheet.

14. The blood component collection system according to claim 12, wherein:
the first gripping member has an engagement groove or an engagement protrusion which is configured to engage with the first gripped member; and
the second gripping member has an engagement groove or an engagement protrusion which is configured to engage with the second gripped member.

15. The blood component collection system according to claim 12, wherein:
the blood component separating device includes a cassette holder which is configured to hold the blood component collection cassette; and
the cassette holder includes an attachment base provided with a cassette mounting groove having a shape that corresponds to an outer peripheral shape of the cassette body, and a lid which is configured to be opened and closed with respect to the attachment base.

16. The blood component collection system according to claim 15, wherein:
the first gripping member is disposed at a position fixed with respect to the attachment base; and
the second gripping member is arranged face-to-face with the first gripping member.

17. The blood component collection system according to claim 15, wherein the attachment base includes an opening configured to receive at least a part of the bulging portion for pressure measurement, and a slit configured to communicate with the opening and allow passage of the second gripped member therethrough.

18. The blood component collection system according to claim 12, wherein the first gripping member comprises a first suction cup and the second gripping member comprises a second suction cup.

19. A blood component collection kit which is configured to be installed in a blood component separating device having a load detection unit, and is equipped with a flow path in which blood is delivered by operation of the blood component separating device, the blood component collection kit comprising:
a bulging structure having a bulging portion for pressure measurement, the bulging portion for pressure measurement bulging in at least one direction of an axis perpendicular to a delivery direction of the flow path,
wherein the bulging structure comprises a filter arranged therein,
wherein the bulging structure is formed of a soft material,
wherein the bulging structure contains in an interior thereof at least a portion of the flow path,
wherein the flow path includes a first line in which the bulging structure is arranged and a second line in which the bulging structure is not arranged,
wherein the second line is spaced apart from the first line on the cassette body and includes a portion that is parallel to the first line,
wherein on one surface of the bulging structure in a thickness direction thereof, there is provided a first gripped member which is configured to be gripped by a first gripping member provided on the blood component separating device,
wherein on another surface of the bulging structure in the thickness direction thereof, there is provided a second gripped member which is configured to be gripped by a second gripping member to which the load detection unit is fixed,
wherein the first gripped member comprises a first base portion having a first curved surface over an entirety of the first base portion,
wherein the first curved surface conforms to the one surface of the bulging structure,
wherein the second gripped member comprises a second base portion having a second curved surface over an entirety of the second base portion, and
wherein the second curved surface conforms to the another surface of the bulging structure.

20. A flow path internal pressure detection method of detecting an internal pressure of a flow path of a blood component collection cassette installed in a blood component separating device configured to collect blood components,
wherein the blood component collection cassette comprises a cassette body with the flow path formed therein,
wherein the cassette body comprises a bulging structure having a bulging portion for pressure measurement, the bulging portion for pressure measurement bulging in a cassette thickness direction on at least one surface of the cassette body,
wherein the bulging structure comprises a filter arranged therein,
wherein the bulging structure is formed of a soft material,
wherein the bulging structure contains therein at least part of the flow path,
wherein the flow path includes a first line in which the bulging structure is arranged and a second line in which the bulging structure is not arranged, and
wherein the second line is spaced apart from the first line on the cassette body and includes a portion that is parallel to the first line,
the flow path internal pressure detection method comprising:
gripping a first gripped member provided on one surface of the bulging structure in a thickness direction thereof, by a first gripping member that is provided on the blood component separating device, and gripping a second gripped member provided on another surface of the bulging structure in the thickness direction, by a second gripping member that is provided on the blood component separating device;

measuring a load applied to a load detection unit fixed to the second gripping member, in a state in which the first gripped member is gripped by the first gripping member, the second gripped member is gripped by the second gripping member, and blood is being delivered to the bulging structure; and calculating the internal pressure of the flow path, based on the measured load, wherein the first gripped member comprises a first base portion having a first curved surface over an entirety of the first base portion, wherein the first curved surface conforms to the one surface of the bulging structure, wherein the second gripped member comprises a second base portion having a second curved surface over an entirety of the second base portion, and wherein the second curved surface conforms to the another surface of the bulging structure.

* * * * *